United States Patent
Niwa et al.

(10) Patent No.: US 9,713,528 B2
(45) Date of Patent: Jul. 25, 2017

(54) INTRAOCULAR LENS INSERTION DEVICE

(71) Applicant: KOWA COMPANY, LTD., Nagoya-shi, Aichi (JP)

(72) Inventors: Kazuharu Niwa, Nagoya (JP); Yasuhiko Suzuki, Hashima-gun (JP); Masayoshi Tanaka, Nagoya (JP)

(73) Assignee: KOWA COMPANY, LTD., Nagoya (JP)

( * ) Notice: Subject to any disclaimer, the term of this patent is extended or adjusted under 35 U.S.C. 154(b) by 0 days.

(21) Appl. No.: 15/140,108

(22) Filed: Apr. 27, 2016

(65) Prior Publication Data
US 2016/0278911 A1 Sep. 29, 2016

Related U.S. Application Data

(62) Division of application No. 13/509,467, filed on Jun. 8, 2012, now abandoned.

(51) Int. Cl.
*A61F 2/16* (2006.01)

(52) U.S. Cl.
CPC .... *A61F 2/167* (2013.01); *A61F 2002/16905* (2015.04)

(58) Field of Classification Search
CPC ...... A61F 2/167; A61F 2/1662; A61F 2/1672; A61F 2/1675; A61F 2/1678; A61F 2/14; A61F 2/16
USPC ......................................... 623/6.12; 606/107
See application file for complete search history.

(56) References Cited

U.S. PATENT DOCUMENTS

| | | | |
|---|---|---|---|
| 7,156,854 B2 | 1/2007 | Brown et al. | |
| 7,335,209 B2 | 2/2008 | Meyer | |
| 2003/0050646 A1 | 3/2003 | Kikuchi et al. | |
| 2009/0171365 A1 | 7/2009 | Tanaka | |
| 2010/0130985 A1* | 5/2010 | Tanaka | A61F 2/1678 606/107 |
| 2010/0161049 A1 | 6/2010 | Inoue | |

FOREIGN PATENT DOCUMENTS

| | | | |
|---|---|---|---|
| EP | 2 072 025 A1 | 6/2009 | |
| JP | H08-505540 A | 6/1996 | |
| JP | 2003-070829 A | 3/2003 | |
| JP | 2004-351196 A | 12/2004 | |
| JP | WO 2008029498 A1 * | 3/2008 | ........... A61F 2/1678 |

(Continued)

OTHER PUBLICATIONS

English translation of JP-A-2009-18009.*

(Continued)

*Primary Examiner* — Kathleen Holwerda
*Assistant Examiner* — Socrates L Boutsikaris
(74) *Attorney, Agent, or Firm* — Oliff PLC

(57) ABSTRACT

An intraocular lens insertion device having a configuration in such a manner that, with the displacement of a haptic toward the convex side of an optical portion, which can be deformed in a curved shape, restricted by an engaging part provided to the tip part of a plunger, the haptic is deformed in a curved shape in the direction in which the haptic approaches the optical portion. The configuration allows, when the intraocular lens is pushed out by the plunger, the haptic to enter a gap formed on the concave side of the optical portion which has been deformed in a curved shape.

1 Claim, 22 Drawing Sheets

(56) References Cited

FOREIGN PATENT DOCUMENTS

JP   2009-018009 A    1/2009
WO   2009/095975 A1   8/2009

OTHER PUBLICATIONS

Dec. 31, 2015 Office Action issued in U.S. Appl. No. 13/509,467.
Jun. 4, 2014 Extended European Search Report issued in European Patent Application No. 09851417.7.
Jun. 12, 2012 International Preliminary Report on Patentability issued in International Application No. PCT/JP2009/006173.
Dec. 22, 2009 International Search Report issued in International Patent Applicatio No. PCT/JP2009/006173.

* cited by examiner

A—A

B—B

C—C

A—A

B—B

C—C

INTRAOCULAR LENS INSERTION DEVICE

The present application is a divisional application of application Ser. No. 13/509,467 filed Jun. 8, 2012, which is a U.S. national stage application of PCT/JP2009/006173 filed Nov. 17, 2009. The disclosures of each of these prior applications are incorporated by reference herein in their entirety.

TECHNICAL FIELD

The present invention relates to an intraocular lens insertion device used for inserting an intraocular lens into the eye.

BACKGROUND ART

From the past, with cataract surgery and the like, a method has been used for which the intracapsular crystalline lens is extracted through an incision provided in ocular tissue such as the cornea (sclera) or anterior capsule of the lens or the like, and after removal, an intraocular lens substituted for that crystalline lens is inserted into the eye using that incision, and arranged within the capsule.

With this intraocular lens surgical operation method, there has been used an intraocular lens insertion device as noted in Patent Document 1 (Published Unexamined Japanese Patent Application No. JP-A-2003-70829) and Patent Document 2 (Published Unexamined Japanese Patent Application No. JP-A-2004-351196). With these intraocular lens insertion devices, the insertion tube part provided at the tip of the device main unit is made to be inserted and enter into the eye through the eye incision, and in a state with the intraocular lens deformed to be smaller within the device main unit, it is made to be extruded into the eye from the tip opening of the insertion tube part. Then, the intraocular lens is arranged within the capsule by the intraocular lens which was extruded into the eye expanding by its own restoration force within the capsule. If this kind of intraocular lens insertion device is used, it is possible to keep the incision small, making it possible to reduce the trouble required for the surgical operation and also possible to reduce the occurrence of postoperative astigmatism and the risk of infection.

As described above, with the intraocular lens insertion device, by the intraocular lens set on a stage provided in the device main unit being moved by the plunger while being pushed toward the insertion tube part, the intraocular lens is made to be extruded into the eye from the insertion tube part tip opening. It is typical for the intraocular lens to be set on a stage in a state with a pair of haptics formed projecting on the optical portion in a state extended facing front and back in the movement direction of the intraocular lens by the plunger. Because of that, when extruding the intraocular lens using the plunger, first, the plunger contacts the haptic (back haptic) extending in the backward movement direction of the intraocular lens, and by the force applied from the plunger being transmitted to the optical portion via the back haptic, the entire intraocular lens is moved toward the insertion tube part.

However, when the entire intraocular lens is pushed via the back haptic and extruded forward to the insertion tube part by the plunger, there is the risk of the back haptic coming off from the plunger pressing surface (tip surface). It is hard for a practitioner to know whether the back haptic has come off the plunger pressing surface. Because of that, by continuing to press the pressing member as is, the back haptic that has come off the plunger pressing surface becomes sandwiched between the inner periphery surface of the insertion tube part that gradually becomes smaller toward the extrusion front and the plunger outer peripheral surface. This sandwiching may cause damage to the back haptic as well as the risk of the plunger pushing operation resistance becoming large, causing problems with the intraocular lens procedure.

In Published Unexamined Japanese Patent Application No. JP-A-2009-18009 (Patent Document 3), proposed is an intraocular lens insertion device with a constitution for which a groove opened at the outer peripheral surface is formed on the tip part of a plunger, and the back haptic that has come off the plunger tip surface is housed inside that groove. However, it is difficult to reliably house the back haptic inside the narrow width groove, and also continue to maintain that housed state throughout the intraocular lens extrusion operation. Also, the back haptic that has come off from the groove formed on the plunger outer peripheral surface is wrapped around the plunger outer peripheral surface. This causes the problem that it can enter between the plunger outer peripheral surface and the insertion tube part inner periphery surface, so it was not a satisfactory product.

BACKGROUND ART DOCUMENTS

Patent Documents

Patent Document 1: JP-A-2003-70829
Patent Document 2: JP-A-2004-351196
Patent Document 3: JP-A-2009-18009

SUMMARY OF THE INVENTION

Problem the Invention Attempts to Solve

The present invention has been developed in view of the circumstances described above as the background, and it is one object of the present invention to provide an intraocular lens insertion device with a novel constitution, which makes it possible to skillfully control the movement of the haptic when extruding the intraocular lens with the plunger, and to avoid problems such as damage to the haptic and the like due to the haptic being sandwiched between the plunger and the device main unit.

Means for Solving the Problem

A first mode of the present invention provides an intraocular lens insertion device comprising: a tube shaped device main unit arranged in which is set an intraocular lens having a pair of haptics projecting from an optical portion; a plunger adapted to be inserted into the device main unit from a back side in an axial direction thereof and attached to the device main unit; a stage arranged on which the intraocular lens is set being provided in an intermediate part of the axial direction of the device main unit; and a tapered insertion tube part formed facing a front side in the axial direction from the stage so that the intraocular lens set on the stage is able to be inserted into an eye by being moved in an axial forward direction of the device main unit by the plunger and by being transformed to be smaller and extruded through the insertion tube part, the intraocular lens insertion device being characterized in that: the intraocular lens is adapted to be set on the stage in a state with the pair of haptics in a state extending from the optical portion facing forward and backward in the axial direction of the device main unit, and by the plunger moving in the axial forward direction of the device main unit, the optical portion is deformed to a curved shape which becomes convex facing an outer peripheral side of the insertion tube part, and a tip part of the plunger that presses the intraocular lens is provided with an engaging part that is adapted to be engaged with the haptic extending from the optical portion in an axial backward direction of the device main unit, suppressing displacement of the haptic to a side for which the optical portion is curved and deformed to be convex.

According to the first mode, when the intraocular lens is extruded by the plunger, the haptic to which the plunger tip part contacts, specifically, the haptic extending from the optical portion to the device main unit backward axial direction (back haptic) is curved and deformed in the direction approaching the optical portion, while the displacement of the back haptic to the convex side of the curved and deformed optical portion is regulated by the engaging part provided on the plunger tip part. Owing to this arrangement, when the intraocular lens is deformed to be small and extruded through the insertion tube part, the back haptic enters a gap formed on the inside (concave side) of the curved and deformed optical portion. As a result, when the intraocular lens is extruded by the plunger, it is possible to make skillful use of the gap formed at the concave side of the optical portion and house the back haptic therein, making it possible to avoid the problem of damage on the back haptic being sandwiched between the plunger and the device main unit.

A second mode of the present invention provides the intraocular lens insertion device according to the first mode, wherein by the intraocular lens being moved forward by the plunger in the axial direction of the device main unit, the optical portion is deformed to be in a curved shape that is convex facing above or below the stage, and a pressing part is provided so that, with the intraocular lens in a state set on the stage, the pressing part pushes the haptic extending from the optical portion in the axial backward direction of the device main unit in an opposite direction from above or below the stage for which the optical portion is deformed and curved to become convex, and causes deformation and displacement in relation to the optical portion.

With the second mode, during extrusion of the intraocular lens by the plunger, it is possible to do pressing deformation and displacement of the back haptic of the intraocular lens set on the stage so as to be relatively displaced to the overlapping surface side of the optical portion in advance. By doing this, along with extrusion of the intraocular lens, it is possible to have the back haptic more reliably and smoothly enter the gap formed at the concave side of the curved and deformed optical portion.

The pressing part noted in this mode can be provided on the device main unit, or can be constituted as a separate member attached to the device main unit. It is also possible to constitute it with a special engaging part provided on the tip part of the plunger. By directly forming on the device main unit and constituting with the engaging part, it is possible to reduce the number of parts. When constituting as a separate member attached to the device main unit, for example if it is a preset type intraocular lens insertion device provided in a state for which the intraocular lens is set on the stage in advance, using a support member provided with projections for positioning and supporting the intraocular lens attached to the device main unit, it is possible to form a projection type pressing part for pressing the haptic on the concerned support member.

A third mode of the present invention provides the intraocular lens insertion device according to the first or second mode, wherein by the intraocular lens being moved forward by the plunger in the axial direction of the device main unit, the optical portion is deformed to the curved shape which is convex facing above or below the stage, and at the tip part of the plunger, a step surface is formed so as to project further in the axial direction at one side of above or below the stage for which the optical portion is curved and deformed to be convex than an other side, and by the haptic being engaged with the step surface, the engaging part that regulates the displacement of the haptic is constituted.

With the third mode, when the plunger is moved in the axial forward direction and touches the back haptic of the intraocular lens, the projecting part of the tip part of the plunger advances to overlap without touching the back haptic, and the non-projecting part of the tip part of the plunger touches the back haptic and starts pushing. Then, the uplift of the back haptic (displacement to the convex side of the curved and deformed optical portion) is regulated by the engaging action of the plunger on the step surface. By doing this, when the plunger presses on the intraocular lens and moves it forward, overlapping of the haptic on the convex side (outer surface) of the curved optical portion is prevented, and it is possible to guide entry to the concave side gap of the optical portion.

A fourth mode of the present invention provides the intraocular lens insertion device according to any one of first through third modes, wherein the intraocular lens set on the stage is constituted as one piece for which the pair of haptics are formed integrally with the optical portion.

Specifically, the present invention can also of course be applied to intraocular lens insertion devices such as of a three piece constitution or the like whereby a haptic formed separately from the optical portion is attached later to the optical portion. Preferably, the present invention is applied to an intraocular lens insertion device used for doing insertion surgery of an intraocular lens of a one piece constitution as noted in this mode. After all, with an intraocular lens of a one piece constitution, the haptic is formed with the same soft material as the optical portion, so compared to intraocular lenses with a three piece constitution for which there are many cases of the haptic being formed from a harder material than the optical portion, the haptic rigidity is lower, and the haptic cross section area is larger. Accordingly, when the intraocular lens is extruded by the plunger, it is necessary to secure a large space to avoid the haptic being sandwiched between the device main unit and the plunger. In light of that, a space for allowing the haptic to escape was ensured by skillfully using the gap formed on the inside of the curved and deformed optical portion. With this arrangement, even with a one-piece constitution intraocular lens, when extruding through the insertion tube part, sandwiching of the haptic between the plunger outer peripheral surface and the insertion tube part inner periphery surface is prevented, making it possible to effectively protect the haptic.

A fifth mode of the present invention provides the intraocular lens insertion device according to the any one of first through fourth modes, wherein provided on the device main unit is a deformation guide member that folds and deforms the optical portion in a mountain shape or valley shape for which one of above or below the stage becomes convex using a ridge line or valley line extending in a movement direction.

With the fifth mode, it is possible to give further stability to the curved shape which is convex in the target direction in relation to the intraocular lens optical portion. With this arrangement, when moving the intraocular lens forward, it is possible to form the gap at the concave side of the curved optical portion with more stability, and possible to more reliably enter the back haptic in that gap.

A sixth mode of the present invention provides the intraocular lens insertion device according to the fifth mode, wherein the deformation guide member is constituted by a deformation guide part that interferes with the intraocular lens moving within the insertion tube part and that gradually deforms the optical portion of the intraocular lens along with movement within the insertion tube part.

With the sixth mode, in a state with the intraocular lens set in the stage, it is not necessary for the optical portion to be curved and deformed in advance, and it is also not necessary to do a special operation on the stage to do curving and deformation at one time. Because of that, for example by setting the intraocular lens placed flat on the stage, by simply the operation of extruding it through the insertion tube part using the plunger, it is possible to do a procedure curving and extruding the optical portion without needing to do a special operation for curving the optical portion. As a result, the work of the procedure for setting the intraocular lens on the stage and extruding is easier. Note that the intraocular lens can be provided in a state set on the stage in advance, or the intraocular lens can be provided separately from the intraocular lens insertion device, and the intraocular lens can be set in the stage at the time of the procedure.

Effect of the Invention

According to the present invention, the displacement of the back haptic to the convex side of the curved and deformed optical portion is regulated by the engaging part provided on the tip part of the plunger, and the back haptic is curved and deformed in the direction approaching the optical portion. This makes it possible to smoothly enter the back haptic in the gap formed in the concave side of the curved and deformed optical portion. As a result, when the intraocular lens is deformed to be small and extruded through the insertion tube part, it is possible to avoid the problem of damage such as of the back haptic being sandwiched between the plunger outer peripheral surface and the insertion tube part inner periphery surface.

EMBODIMENTS FOR CARRYING OUT THE INVENTION

Embodiments of the present invention will be explained below with reference to attached drawings.

Figure 1:
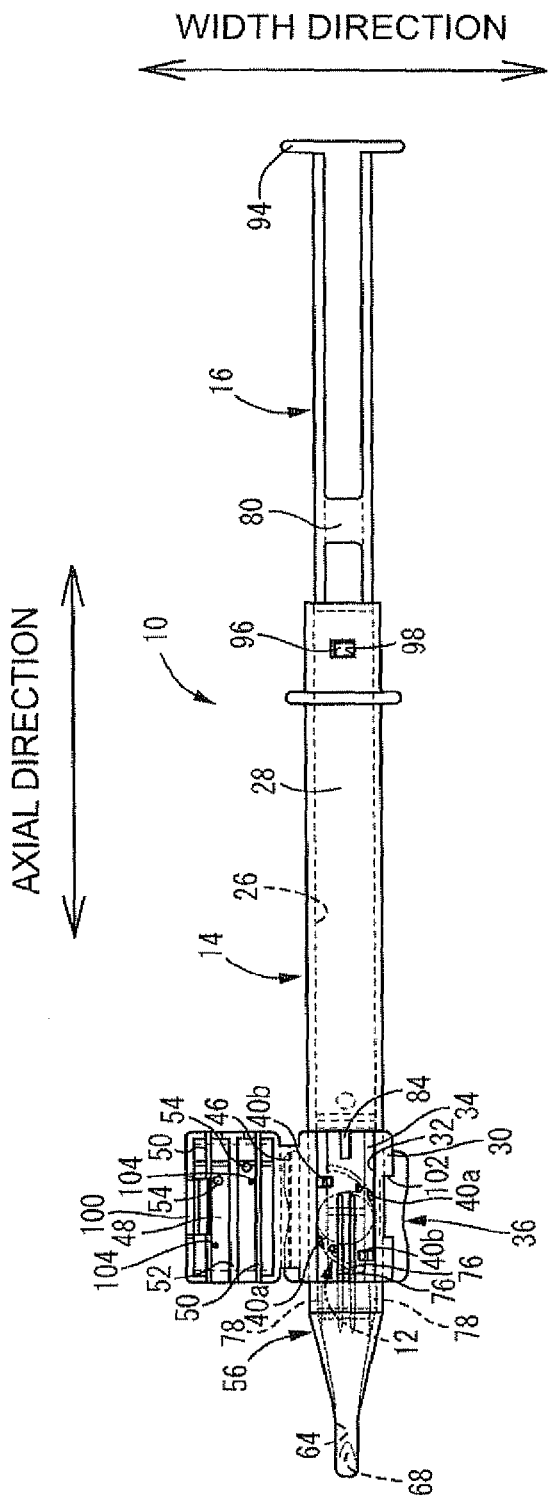
FIG. 1 is a plan view of an intraocular lens insertion device as a first embodiment of the present invention.
Figure 2:
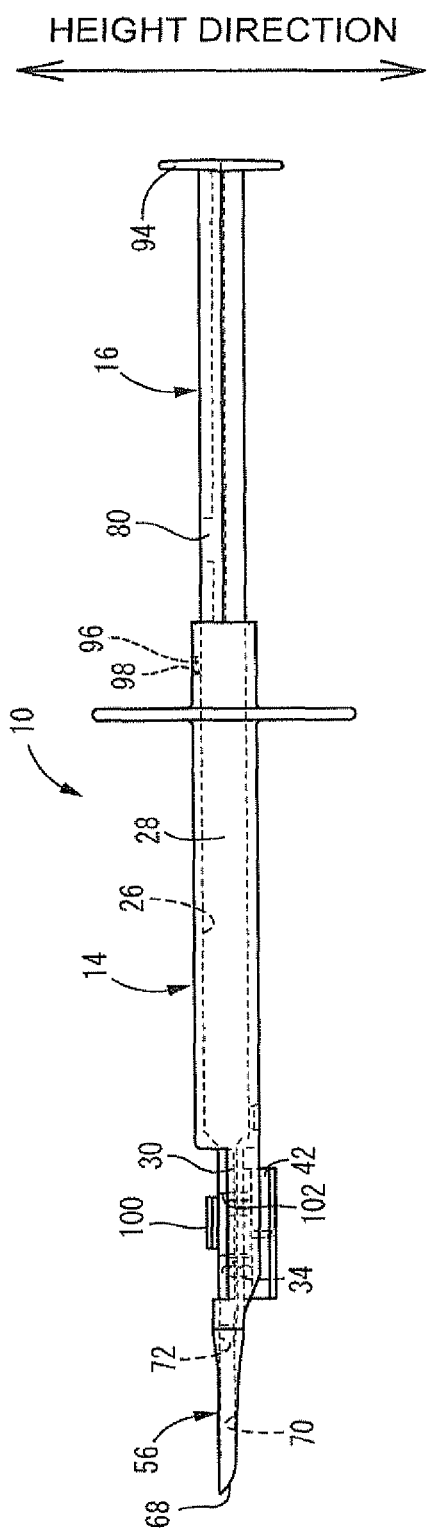
FIG. 2 is a side view of the intraocular lens insertion device shown in FIG. 1.

FIG. 1 and FIG. 2 show an intraocular lens insertion device 10 as a first embodiment of the present invention. The intraocular lens insertion device 10 is constituted with a plunger 16 attached inserted in the roughly tube shaped device main unit 14 in which the intraocular lens 12 described later is set. With the description below, the leftward direction in FIG. 1 is the forward axial direction of the intraocular lens insertion device 10, and the rightward direction in FIG. 1 is the backward axial direction. Also, the vertical direction of FIG. 2 is used as the height direction, and also, the vertical direction in FIG. 1 is used as the width direction.

Figure 3:
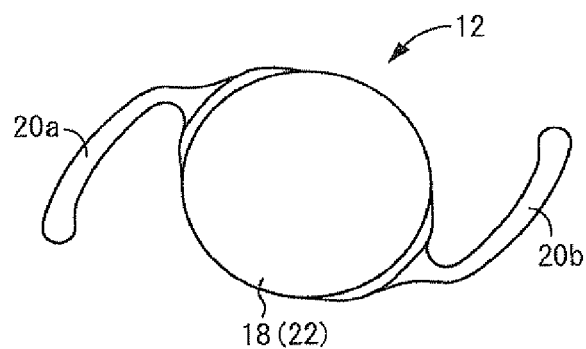
FIG. 3 is a plan view showing an intraocular lens set in the device main unit of the intraocular lens insertion device shown in FIG. 1.
Figure 4:
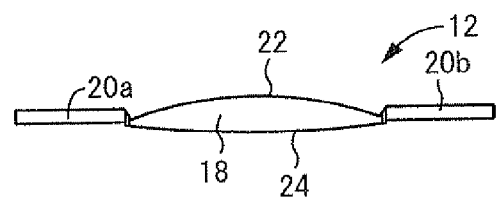
FIG. 4 is a side view of the intraocular lens shown in FIG. 3.

In more detail, the intraocular lens 12 is an intraocular lens 12 that is well know from the past, and as shown in FIG. 3 and FIG. 4, has a one piece constitution for which the pair of haptics 20a, 20b are formed integrally with the optical portion 18. The intraocular lens 12 can also have a three piece constitution for which the haptic formed separately from the optical portion is attached later to the optical portion.

The optical portion 18 gives the optical characteristics, and the item in the drawing which is in a state arranged inside the crystalline lens capsule has optical portion front surface 22 positioned at the cornea side within the capsule and optical portion back surface 24 positioned at the vitreous body side being formed with mutually different curvatures.

The pair of haptics 20a, 20b project from the outer periphery part facing opposite in the radial direction of the optical portion 18, and sandwich the optical portion 18 while facing the outer peripheral side for which they are roughly facing opposite to each other. Also, the projecting tip parts of the pair of haptics 20a, 20b extend curving toward the same direction mutual to each other in the peripheral direction of the optical portion 18.

The device main unit 14 in which this kind of intraocular lens 12 is set is formed by a hard synthetic resin material having optical transparency, and is equipped with a main unit tube part 28 for which a center hole 26 is formed extending straight in the axial direction with a roughly rectangular cross section shape. A stage 30 is provided further in the axial forward direction than the main unit tube part 28.

On the stage 30, a concave groove 32 extending in the axis direction opening upward is formed in a state communicating with the center hole 26 of the main unit tube part 28. Specifically, the stage 30 is in a state with one long side part removed at the cross section of the main unit tube part 28, and is in a form so as to extend facing the axial direction forward. Then, the bottom surface of the concave groove 32 is used as a lens placement surface 34, and this lens placement surface 34 is a flat surface that broadens in the width dimension that is slightly larger than the outer radial dimension of the optical portion 18 of the intraocular lens 12. Also, the lens placement surface 34 length dimension (axial direction dimension) is slightly larger than the maximum length dimension containing the intraocular lens 12 haptics 20a, 20b (FIG. 3 left and right direction dimensions). By doing this, at roughly the center part of the lens placement surface 34, the intraocular lens 12 is made to be placed flat in a free state without touching both side walls of the concave groove 32. Also, in this placed-flat state, if an attempt is made to rotate the intraocular lens 12 around the center axis of the optical portion 18, the haptics 20a, 20b touch both side walls of the concave groove 32 and rotation is prevented.

Also, on the stage 30, a support member 36 is attached with the ability to be removed from the outer periphery surface opposite the lens placement surface 34. The support member 36 is equipped with a base plate part 38 overlapping at the outer surface of the bottom wall part of the concave groove 32 forming the lens placement surface 34 (see FIG. 14), and on this base plate part 38 are formed a plurality of acting projections 40a, 40a, 40b, 40b which project above the overlapping surface to the bottom wall part of the concave groove 32. Also, an operating piece 42 which broadens extending toward the outside opposite to the surface overlapping on the bottom wall part of the concave groove 32 is formed as a single unit on the base plate part 38.

Then, with the support member 36, its base plate part 38 is attached to the main unit tube part 28 so as to overlap from the outside in relation to the bottom wall part of the concave groove 32 of the stage 30. Also, a plurality of through holes 44a, 44a, 44b, 44b are formed on the bottom wall part of the stage 30 to which the support member 36 is attached. Then, the plurality of acting projections 40a, 40a, 40b, 40b provided projecting on the support member 36 attached to the main unit tube part 28 project to the inner surface of the bottom wall part of the stage 30 through the through holes 44a, 44a, 44b, and 44b.

The number, shape, and forming position of the acting projections 40 are not particularly restricted. Preferably, taking into consideration the shape, size, etc. of the intraocular lens 12 set on the stage 30, setting can be done as appropriate by supporting the intraocular lens 12 held in a state floating above from the bottom wall part of the stage 30, and positioning the intraocular lens 12 within the stage 30, or by preventing displacement of the plunger 16 in the pushing direction in relation to the main unit tube part 28. Then, each position and each shape of the plurality of through holes 44 is set on the stage 30 corresponding to each position and each shape of that plurality of acting projections 40.

Specifically with this embodiment, two acting projections 40a, 40a are provided for positioning the intraocular lens 12. The intraocular lens 12 is made to be positioned by the two positioning projection parts provided projecting at the projection tip surface of each acting projection 40a sandwiching the haptics 20a, 20b from both sides of the peripheral direction of optical portion 18 and positioning them.

Also, with the two acting projections 40b, 40b respectively in a state inserted in through holes 44b, 44b, an engaging claw 41 provided on the side surface is engaged with the lens placement surface 34. Thus, the support member 36 is attached to the device main unit 14.

As a releasable attachment mechanism for stably holding the support member 36 in an attached state to the main unit tube part 28, in addition to an item that uses the engaging claw 41 provided on the acting projection 40b, it is also possible to do something like press fit the acting projection 40 into the through hole 44 and use the frictional force of the two items.

Meanwhile, a lid unit 48 connected with the stage 30 by a hinge part 46 is provided at one width direction side of the stage 30 (upward side in FIG. 1), and the upper side opening of the concave groove 32 is able to be covered by the lid unit 48. On the lid unit 48, in a state with the upper side opening of the concave groove 32 covered, a pair of left and right guide plate units 50, 50 are provided extending in the axial direction projecting toward the lens placement surface 34. Also, on the lid unit 48, between the pair of left and right guide plate units 50, 50, a center guide plate unit 52 extending in parallel to the left and right guide plate units 50, 50 is provided projecting in the same direction as the left and right guide plate units 50, 50. With this arrangement, in a state with the lid unit 48 closed, excessive displacement upward of the intraocular lens 12 is restricted, and it is possible to smoothly guide the intraocular lens 12 to the nozzle part 56 described later.

Also, in a state with the lid unit 48 closed, two pressing parts 54 projecting facing the lens placement surface 34 are provided on the lid unit 48. These two pressing parts 54, 54 are each formed as a single unit with the lid unit 48, and they have the same mutual shape and size.

The two pressing parts 54, 54 each exhibit a cylinder shape, and in a state with the lid unit 48 closed, the projection tip surface is a flat surface that broadens in parallel with the lens placement surface 34. The projection tip surfaces of the two pressing parts 54, 54 are at the same height position. The outer radial dimension of the two pressing parts 54, 54 is greater than the width dimension of the haptic 20b.

Also, in a state with the lid unit 48 closed, the two pressing parts 54, 54 are provided at a position in contact with the haptic 20b positioned in the backward movement direction of the intraocular lens 12. In particular with this embodiment, the two pressing parts 54, 54 are provided so as to be in contact with the haptic 20b at a position for which the contact position of the plunger 16 on the haptic 20b is a position for which it is sandwiched in the groove width direction of the concave groove 32.

Then, when the lid unit 48 is closed, the two pressing parts 54, 54 press the haptic 20b of the intraocular lens 12 that is placed flat on the lens placement surface 34 in a free state against the lens placement surface 34. With this arrangement, the haptic 20b deforms to the lens placement surface 34 side in relation to the optical portion 18 compared to when in a free state. Specifically, by the haptic 20b being pressed by the two pressing parts 54, 54, compared to when in a free state, it is displaced in an direction approaching the lens placement surface 34.

The pressing parts 54 shape and size, forming position, number installed, and the like are not limited to the mode shown in the illustrations. For example, it is also possible to have one pressing part 54 formed only further to one groove width direction side of the concave groove 32 than the contact position of the plunger 16 on the haptic 20b, and to have one pressing part 54 formed only at the other groove width direction side.

Also, from the perspective of ensuring the pressing surface area in relation to the haptic 20b, the pressing part 54 preferably has surface contact on the haptic 20b, but it does not absolutely have to have surface contact. For example, if the pressing part 54 has a tapered shape such as a conical shape, hemispheric shape, or gabled roof shape, or a shape such as a hipped roof shape, it is also possible to have point contact or line contact of the pressing part 54 on the haptic 20b.

When providing a plurality of pressing parts 54, the shape and size of each pressing part 54 is set taking into consideration the contact position on the haptic 20b, and they can be the same or different from each other. Note that when the projection height of the plurality of pressing parts 54 are the same, it is possible to make the haptic 20b pressed on the lens placement surface 34 side flat by this plurality of pressing parts 54. As is described later, it becomes easy to enter the haptic 20b at the bottom of the step surface 86.

The pressing part 54 does not have to be formed as a single unit with the lid unit 48. It is of course also possible to form a pressing part 54 separately from the lid unit 48 and to attach it to the lid unit 48 later.

Figure 5:
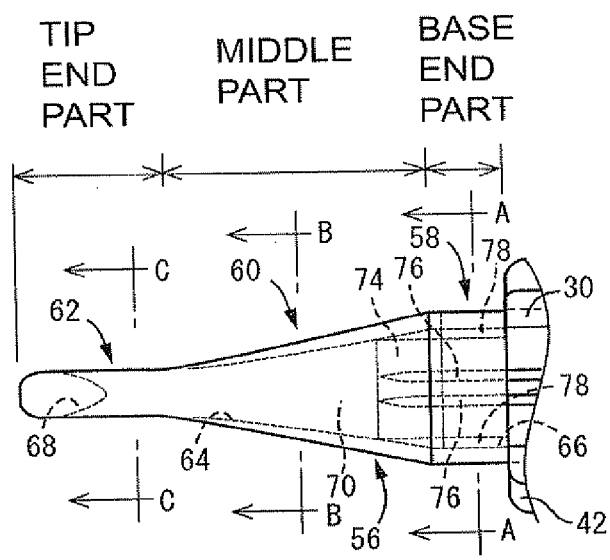
FIG. 5 is an explanatory plan view showing the nozzle part provided on the device main unit of the intraocular lens insertion device shown in FIG. 1.
Figure 6:
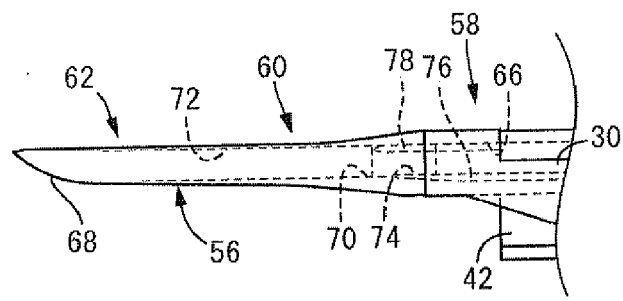
FIG. 6 is an explanatory side view of the nozzle part shown in FIG. 5.

The nozzle part 56 is provided as the insertion tube part further in the axial forward direction than the stage 30 on the device main unit 14. As shown in FIGS. 5 to 7, with the nozzle part 56, the sequence from the stage 30 side is the base end part 58, the middle part 60, and the tip end part 62, and overall this exhibits an external shape that becomes tapered as it goes from the base side to the tip side. The base end part 58 and the tip end part 62 extend straight in the axial direction in a roughly constant cross section shape. Meanwhile, the middle part 60 is a tapered shaped gradually contracting cross section part for which the cross section shape gradually becomes smaller as it goes in the axial forward direction.

Figure 7A:
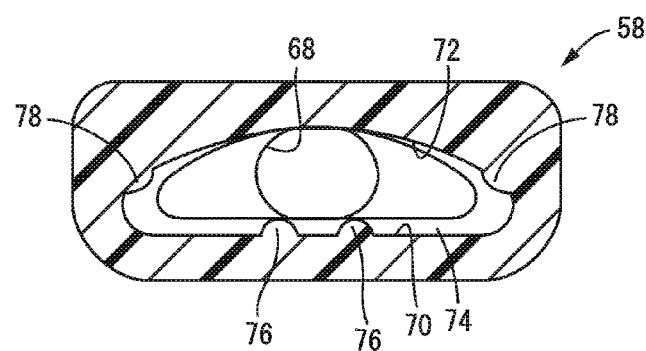
FIGS. 7A-7C are A-A to C-C cross section views of FIG. 5.
Figure 7B:
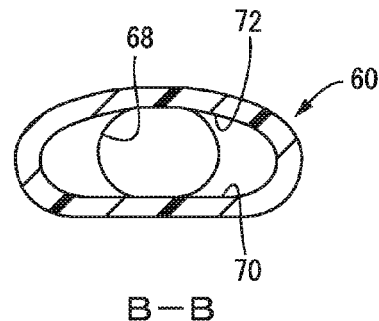
Figure 7C:
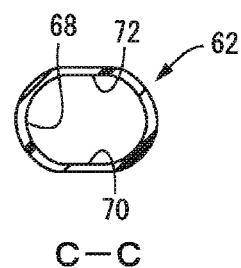

On the nozzle part 56, a through hole 64 is formed extending along the entire length in the axial direction in a state communicating with the concave groove 32, and the width dimension of the base end side opening part 66 of the through hole 64 is roughly the same size as the groove width dimension of the concave groove 32 (width dimension of the lens placement surface 34). Also, the through hole 64 has a half moon shaped or stacked-rice-cake shaped opening cross section at the base end side opening part 66, but the opening cross section is deformed gradually to a roughly oval shape as it goes to the tip end side opening part 68. By doing this, with the intraocular lens 12 in a non-deformed free state, it is difficult to move the middle part 60, and the optical portion 18 is curved and deformed at the stage when delivering to the middle part 60. As shown in FIGS. 7A-7C, the through hole 64 of the nozzle part 56 has a horizontally spreading flat cross section shape for which the vertical direction in FIG. 5 that is the width direction of the stage 30 is the width direction, and the vertical direction in FIG. 6 is the height direction. Also, its flatness ratio (flatness degree) is greater at the base end side opening part 66 than the tip end side opening part 68, and gradually changes at the middle part 60.

Also, formed on the through hole 64 are a bottom surface 70 connected without steps from the lens placement surface 34, and a top surface 72 positioned above the bottom surface 70. On the bottom surface 70, a tilted surface 74 which gradually rises as it goes in the axial forward direction is formed extending across the base end part 58 and the middle part 60. The bottom surface 70 is a flat surface for both side parts of the axial direction sandwiching the tilted surface 74. Meanwhile, the top surface 72 is a flat surface with no steps along the entire length of the axial direction.

A pair of guide rails 76, 76 projecting toward the top surface 72 are formed at the width direction center part of the bottom surface 70 of the base end part 58. The guide rails 76, 76 are projections extending in a straight line in the axial direction across a specified dimension, and their tip parts (axial direction front side end part) are positioned at the tip of the tilted surface 74 (axial direction front end). Note that the tip parts of the guide rails 76, 76 are made to be gradually drawn into the bottom surface 70 as they go toward the tip by rising gradually as the tilted surface 74 goes in the axial forward direction, and have the same height position as the bottom surface 70. Meanwhile, the back end part of the guide rails 76, 76 extend out to the lens placement surface 34 past the back end of the base end part 58. This kind of guide rails 76, 76 are formed roughly parallel to each other separated by a specified distance in the width direction sandwiching the width direction center of the bottom surface 70.

On both end parts of the width direction on the top surface 72 of the base end part 58 are respectively formed side rails 78 projecting toward the bottom surface 70. The side rails 78 project extending in a straight line in the axial direction across a specified dimension, and the tip parts (axial forward direction side tip parts) are in roughly the same axial direction position as the tip parts of the guide rails 76, 76. The tip parts of the side rails 78 are made to be gradually drawn into the inner surface of the nozzle part 56 as it goes to the tip part (axial forward direction), and are made to be equivalent to the inner surface of the nozzle part 56. Meanwhile, the back end parts of the side rails 78 are positioned at the base end side opening part 66 which becomes the back end of the base end part 58. This kind of side rails 78 are formed roughly parallel to each other.

Figure 8:
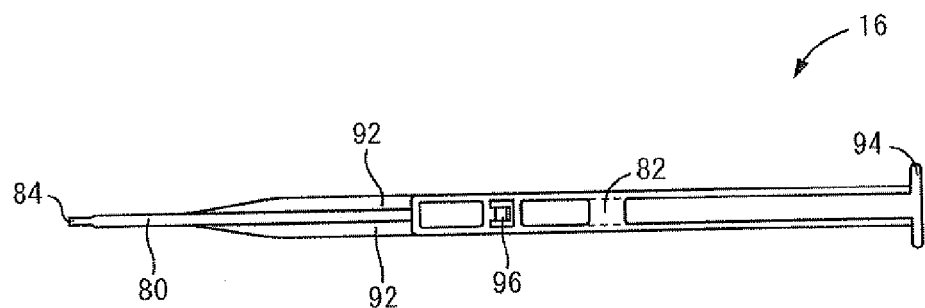
FIG. 8 is a plan view of the plunger constituting the intraocular lens insertion device shown in FIG. 1.
Figure 9:
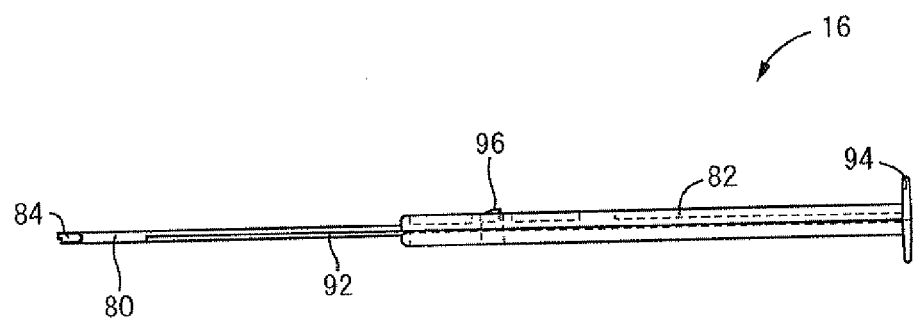
FIG. 9 is a side view of the plunger shown in FIG. 8.

From the axial backward direction of this kind of device main unit 14, the plunger 16 is inserted into the center hole 26 and attached to the device main unit 14. The plunger 16, as shown in FIG. 8 and FIG. 9, exhibits roughly a rod shape, and is equipped with an acting part 80 positioned at the axial direction front side and an insertion part 82 positioned further to the axial direction back side than the acting part 80.

Figure 10:
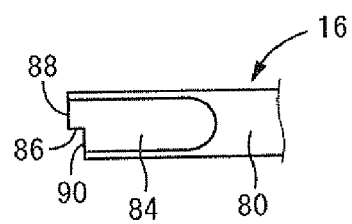
FIG. 10 is an enlarged plan view showing the tip part of the plunger shown in FIG. 8.
Figure 11:
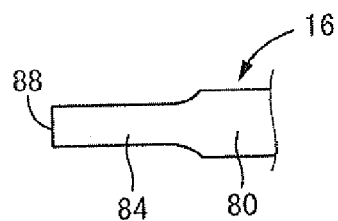
FIG. 11 is an enlarged side view showing the tip part of the plunger shown in FIG. 8.

The acting part 80 has a rod shape extending straight in the axial direction having a roughly oval shaped fixed cross section shape, and as shown expanded in FIG. 10 and FIG. 11, its tip part 84 has smaller width direction (vertical direction in FIG. 11) dimensions than the base end part.

A step surface 86 is formed as the engaging part expanding across a specified length in the axial direction on the tip part 84. Thus, on the tip part 84, an optical portion pressing surface 88 is formed on the height direction top side (open side of the concave groove 32) sandwiching the step surface 86, and also, a haptic pressing surface 90 is formed on the height direction bottom side (bottom side of the concave groove 32, specifically, the lens placement surface 34 side). The optical portion pressing surface 88 is positioned further in the axial forward direction of the plunger 16 than the haptic pressing surface 90.

As long as the step surface 86 axial direction dimension (depth dimension) is of a size for which it can engage with the haptic 20b, it is not particularly limited, but it is preferable to be larger than half the width dimension of the haptic 20b. As is described later, it is possible to realize stable holding down of the haptic 20b by the step surface 86.

As long as the height direction dimension of the haptic pressing surface 90 is of a size for which it can engage with the haptic 20b, it is not particularly limited, but it is preferable that it be larger than the height dimension (thickness dimension) of the haptic 20b. This makes it possible to realize stable holding down of the haptic 20b by the haptic pressing surface 90.

Note that thin plate shaped reinforcing ribs 92 are provided on both width direction sides of the acting part 80, ensuring the strength of the acting part 80.

Meanwhile, the insertion part 82 has a rod shape that extends straight with an overall letter H cross section, and at its back end, formed as a single unit broadening in the axis right angle direction is a pressing plate 94 which adds pushing force when pushing the plunger 16.

This kind of plunger 16 is attached to the device main unit 14 by being inserted in the main unit tube part 28 from the acting part 80 side. Accordingly, the intraocular lens insertion device 10 is obtained. When attaching the plunger 16 to the device main unit 14, the initial position of the plunger 16 in relation to the device main unit 14 is set by the engaging claw 96 provided on the insertion part 82 being engaged with the engaging hole 98 formed on the main unit tube part 28. This plunger 16 is prevented from being extracted from the main unit tube part 28 by the engaging action of the engaging claw 96 in the engaging hole 98, and the pushing direction to the main unit tube part 28 can be displaced using a specified resistance force.

Also, the intraocular lens 12 is set in the intraocular lens insertion device 10 for which the plunger 16 is attached at the initial position in relation to the device main unit 14 as described above.

Figure 12:
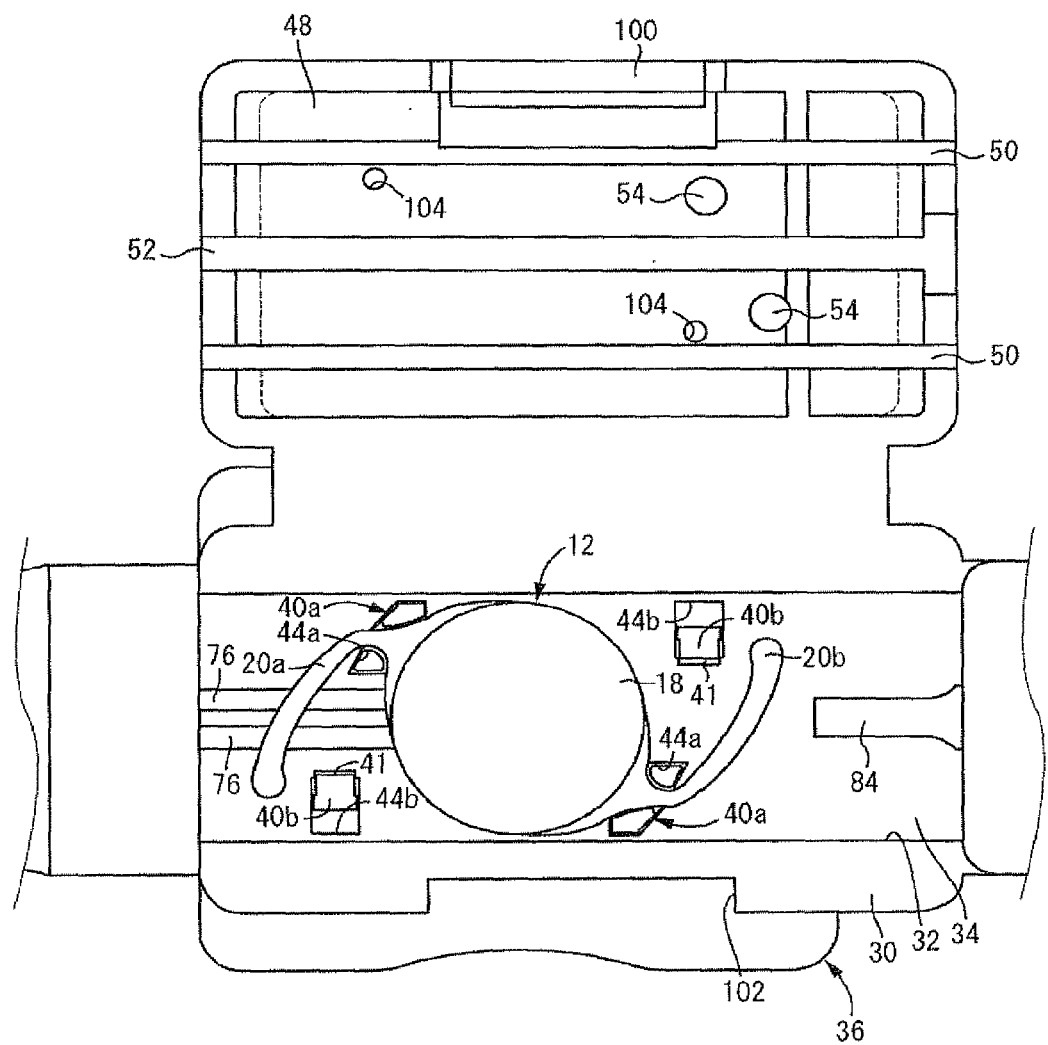
FIG. 12 is an explanatory plan view for describing the state of the intraocular lens being set in the stage of the intraocular lens insertion device shown in FIG. 1.

In specific terms, as shown in FIG. 12, with the device main unit 14, by housing the intraocular lens 12 in the concave groove 32 of the stage 30 opened with the lid unit 48 open, the intraocular lens 12 is arranged in the stage 30. In particular with this embodiment, the intraocular lens 12 is housed in the concave groove 32 with the optical portion back surface 24 on the bottom side, and it is positioned and set by the acting projections 40a, 40a of the support member 36 attached to the stage 30. In this state, the center part of the optical portion back surface 24 of the intraocular lens 12 is placed after making contact with the guide rails 76, 76.

The base end parts of the haptics 20a, 20b of the intraocular lens 12 are placed on the top end surface of the two acting projections 40a, 40a, essentially the entire intraocular lens 12 is brought up from the bottom surface of the concave groove 32, and can be set in a state for which action on the optical portion 18 by the contact stress on the bottom surface is avoided as much as possible.

Also, the intraocular lens 12 positioned by the two acting projections 40a, 40a is held in a free state with acting stress and distortion reduced on the optical portion 18, and the pair of haptics 20a, 20b extend out toward both sides in the axial direction of the device main unit 14 (forward-backward direction). Also, the haptic 20b positioned further to the axial backward direction than the optical portion 18 is positioned slightly separated forward in the extrusion direction from the optical portion pressing surface 88 of the plunger 16 in its initial position.

By overlapping the step surface 86 provided on the tip part 84 of the plunger 16 from the top side on the haptic 20b, it is possible to press the haptic 20b on the lens placement surface 34 side, and to displace the haptic 20b approaching toward the lens placement surface 34. In this case, it is not necessary to provide pressing parts 54 on the lid unit 48.

Figure 13:
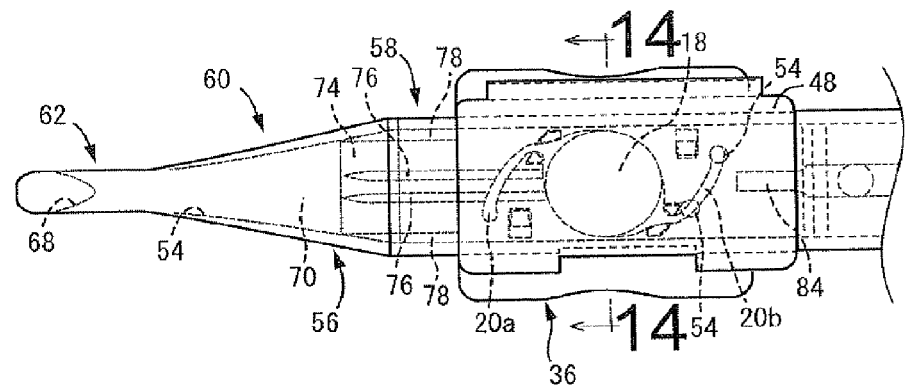
FIG. 13 is an explanatory plan view for describing the state of the lid unit being closed with the intraocular lens insertion device shown in FIG. 1.
Figure 14:
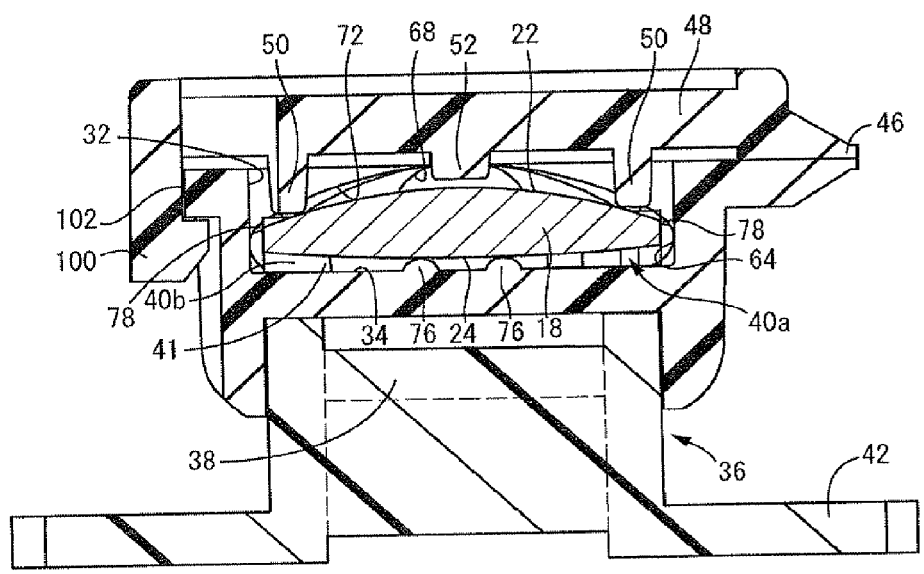
FIG. 14 is an explanatory cross section view corresponding to a cross section view of 14-14 of FIG. 13.
Figure 15:
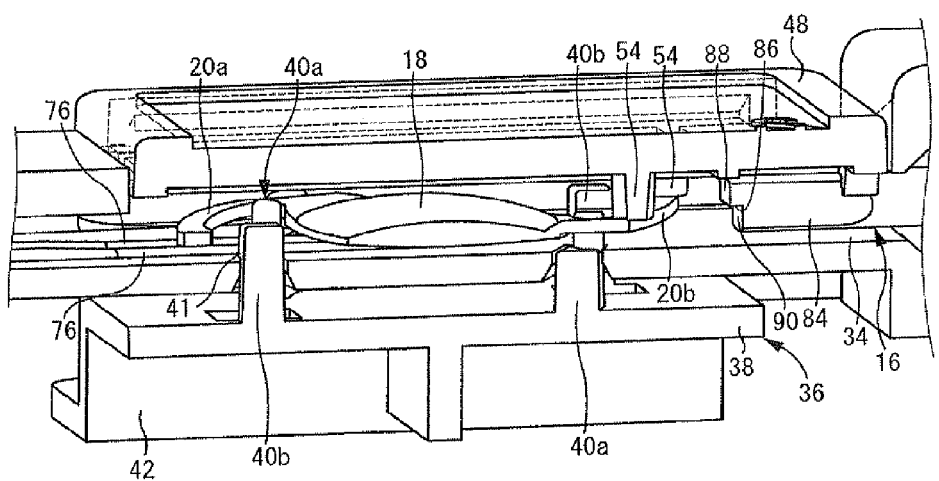
FIG. 15 is a perspective view shown with the side wall part of the stage cut away to describe the state with the lid unit closed with the intraocular lens insertion device shown in FIG. 1.

As described above, after housing the intraocular lens 12 inside the concave groove 32 of the stage 30 in this way, by closing the lid unit 48, the top side opening of the concave groove 32 is covered by the lid unit 48. By doing this, as shown in FIGS. 13 to 15, the intraocular lens 12 is set in a state housed within the device main unit 14. With the lid unit 48 in a closed state, the engaging piece 100 provided on the lid unit 48 is engaged with the engaging notch 102 provided on the stage 30, and the closed state of the lid unit 48 is maintained.

Figure 16:
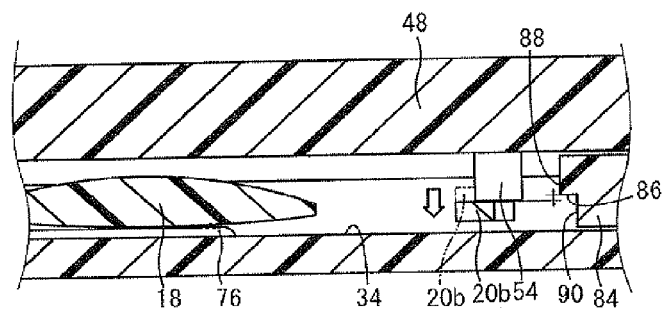
FIG. 16 is an explanatory cross section view for describing the state of the back haptic with the intraocular lens insertion device shown in FIG. 1 being pressed by the pressing part provided on the lid unit.

Also, in a state with the lid unit 48 closed, as shown in FIG. 13, one pressing part 54 is in contact more to the base end side than the contact position of the plunger 16 on the haptic 20*b*, and further to the extension end side than the position positioned by the acting projection 40*a*, and also the other pressing part 54 is in contact further to the extension end side than the contact position of the plunger 16 on the haptic 20*b*. Thus, as shown in FIG. 16, the contact position of the plunger 16 on the haptic 20*b* is positioned further to the bottom side in the height direction than the step surface 86 formed on the plunger 16.

The plunger 16 can also be inserted in the device main unit 14 and set at the initial position before the intraocular lens 12 is housed inside the concave groove 32 of the stage 30, but it is also possible to insert the plunger 16 in the device main unit 14 after the intraocular lens 12 is housed inside the concave groove 32, or furthermore after the lid unit 48 is closed.

After that, the intraocular lens insertion device 10 in which the intraocular lens 12 is set is provided housed and shipped packed in an airtight case or the like. At that time, suitable disinfection or the like is implemented with the processes before or after packing in an airtight case, or with both processes before and after packing.

Incidentally, when inserting the intraocular lens 12 into the eye using the intraocular lens insertion device 10 provided in this way, first, with the intraocular lens insertion device 10 taken out from the packaging at the surgery location, the support member 36 is drawn to under the stage 30, and removed from the device main unit 14. Therefore, the positioning of the intraocular lens 12 by the plurality of acting projections 40*a*, 40*a* formed on the support member 36 is cancelled, and it is possible to move the intraocular lens 12 above the lens placement surface 34 of the stage 30.

A suitable lubricating agent may be injected into the interior of the stage 30 or the nozzle part 56 through an injection hole 104 formed on the lid unit 48. Thus, before extrusion using the plunger 16, it is possible to have the intraocular lens 12 float above from the guide rails 76, 76. As a result, as will be described later, it becomes easier to enter the haptic 20*b* to the inside of the optical portion 18 which has been curved and deformed to a mountain fold state, or to enter the haptic 20*b* below the optical portion 18 before being curved and deformed to a mountain fold state.

When the support member 36 is removed from the device main unit 14, the tip end side opening part 68 of the nozzle part 56 is inserted in the incision provided in the ocular tissue. Then, while maintaining the insertion state of the nozzle part 56 in the incision, the plunger 16 is pushed into the device main unit 14.

Figure 17:
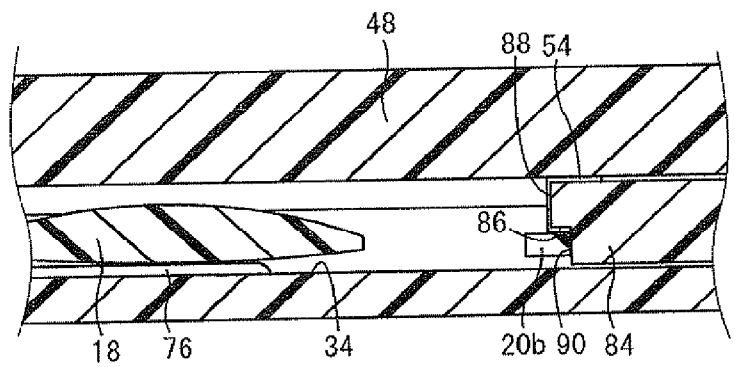
FIG. 17 is an explanatory cross section view for describing the state of the back haptic with the intraocular lens insertion device shown in FIG. 1 entering below the step surface formed on the tip part of the plunger.
Figure 18:
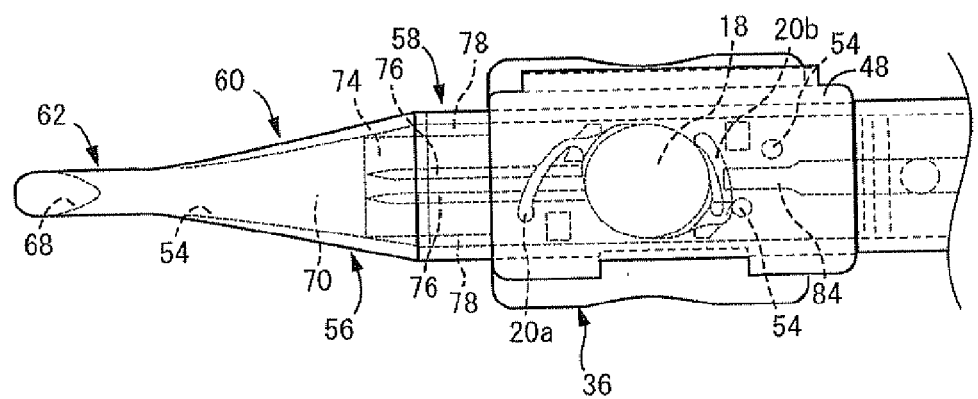
FIG. 18 is an explanatory plan view for describing the back haptic being in a curved and deformed state.

At that time, the contact site of the plunger 16 on the haptic 20*b* is positioned further to the lens placement surface 34 side than the step surface 86 formed on the plunger 16, so when the plunger 16 is pushed into the device main unit 14, as shown in FIG. 17, the haptic 20*b* positioned in the intraocular lens 12 backward axial direction (backward movement direction) enters the bottom side of the step surface 86 formed on the plunger 16, and contacts the haptic pressing surface 90. As a result, as shown in FIG. 18, by the haptic 20*b* being pressed to the optical portion 18 side by the haptic pressing surface 90, it is curved and deformed in the direction approaching the optical portion 18.

When the haptic 20*b* is curved and deformed to the optical portion 18 side to the point that the optical portion 18 is in contact with the outer peripheral surface, the pressing force from the plunger 16 is transmitted via the haptic 20*b* to the optical portion 18. As a result, the overall intraocular lens 12 is moved toward the nozzle part 56 while being pressed by the plunger 16.

In a state with the haptic 20*b* in contact with the haptic pressing surface 90, when the optical portion pressing surface 88 is positioned further in the forward movement direction than the haptic 20*b*, by the optical portion pressing surface 88 of the plunger 16 contacting the outer peripheral surface of the optical portion 18, the pressing force of the plunger 16 is directly transmitted to the optical portion 18. At that time, it is acceptable to have the haptic 20*b* either contact or not contact the outer peripheral surface of the optical portion 18.

For some time after the haptic 20*b* is pressed by the haptic pressing surface 90, the pressing parts 54, 54 push the haptic 20*b* to the lens placement surface 34 side. Therefore, when the haptic 20*b* starts being pressed by the haptic pressing surface 90, a gap is formed between the haptic 20*b* and the step surface 86.

When the haptic 20*b* that moves while being pressed by the plunger 16 is removed from the position at which it is held down by the pressing parts 54, 54, it is displaced to the height direction upper side (open side of the concave groove 32) by its own elasticity. At that time, the step surface 86 is positioned above the haptic 20*b*, so the haptic 20*b* contacts the step surface 86. Therefore, when the haptic 20*b* is pressed by the haptic pressing surface 90, displacement upward in the height direction is prevented by the step surface 86.

Figure 19A:
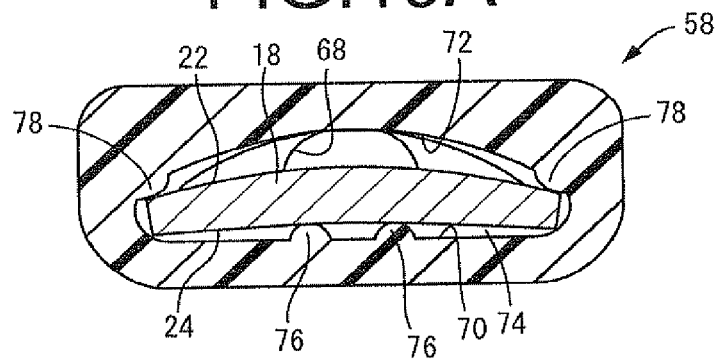
FIGS. 19A-19C are explanatory cross section views for describing the intraocular lens deformed state.

As shown in FIG. 19A, with the intraocular lens 12 delivered to the base end part 58, the center part of the optical portion back surface 24 is in contact with the guide rails 76, 76, and the side rails 78, 78 are in contact with both side end parts in the direction orthogonal to the extrusion direction at the optical portion front surface 22. While external force toward the top surface 72 is applied to the center part of the optical portion back surface 24, external force toward the bottom surface 70 is applied to both side end parts in the direction orthogonal to the extrusion direction at the optical portion front surface 22. As a result, with the optical portion 18 of the intraocular lens 12, the optical portion front surface 22 becomes convex facing the top surface 72 which is positioned at the top side of the vertical direction, and also a ridge line is deformed to a mountain fold extending in the movement direction of the intraocular lens 12. Note that with FIGS. 19A-19C, the state of the optical portion 18 of the intraocular lens 12 being deformed to a mountain fold is illustrated as a model, and an illustration of the haptics 20*a*, 20*b* has been omitted.

Figure 19B:
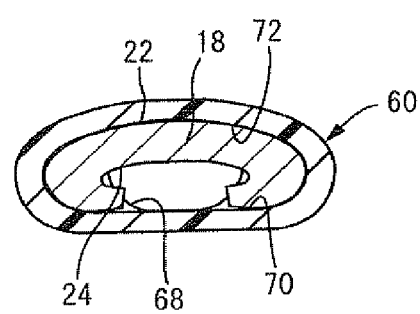
Figure 19C:
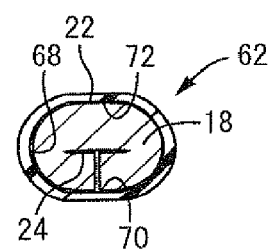

As shown in FIG. 19B, while the intraocular lens 12 for which the initial mountain fold state deformation was applied with the base end part 58 is deformed to be smaller through the middle part 60, it is sent toward the tip end side opening part 68 of the nozzle part 56. At that time, the optical portion 18 is deformed along the internal surface shape of the through hole 64, the mountain fold state advances even further, and the optical portion front surface 22 is rounded in a state contacting the top surface 72. Then, as shown in FIG. 19C, the optical portion 18 is rounded to be small in a roughly oval shape at the tip end part 62 of the nozzle part 56 by the through hole 64 which is gradually made into roughly an oval shape as it goes to the tip end part 62.

Specifically, with this embodiment, a deformation guide member is constituted including a pair of guide rails 76, 76, a pair of side rails 78, 78, and a specially shaped through hole 64 formed on the nozzle part 56, and the deformation guide part is constituted by the pair of guide rails 76, 76 and the pair of side rails 78, 78.

Also, as described above, when the optical portion 18 starts to be deformed to a mountain fold state, a space (gap) appears formed on the optical portion back surface 24 side (concave side) of the optical portion 18 deformed to a mountain fold state at the forward extrusion direction of the plunger 16. When the deformation volume of the optical portion 18 becomes large, as shown as a model in FIG. 20, the haptic 20b engaged with the tip part 84 of the plunger 16 enters the inside (concave side) of the optical portion 18 deformed to a mountain fold state. As a result, the haptic 20b is protected so as to be wrapped by the optical portion 18. Then, the intraocular lens 12 moves within the nozzle part 56 with the haptic 20b wrapped by the optical portion 18 in this way.

Note that the entry of the haptic 20b to the optical portion back surface 24 side of the optical portion 18 is not limited to when the optical portion 18 is deformed to the mountain fold state. For example, it is also possible to have the haptic 20b enter the optical portion back surface 24 side before the optical portion 18 is deformed to the mountain fold state by using the float up volume of the optical portion 18 guide rails 76, 76 or the push-in volume of the haptic 20b by the pressing parts 54, 54 before the plunger 16 pushes the haptic 20b.

Figure 20:
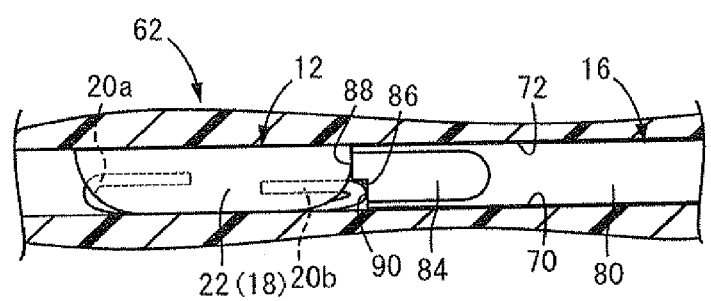
FIG. 20 is an explanatory cross section view showing the state of each haptic entered in the inside of the curved and deformed optical portion.

Also, the haptic 20a positioned at the front of the intraocular lens 12 extrusion direction is entered into the interior of the rounded optical portion 18 along with rounding of the optical portion 18 according to the through hole 64 inner surface shape. Thus, as shown in FIG. 20, a tucking state is manifested on the intraocular lens 12 inside the through hole 64.

Then, in a state with the haptics 20a, 20b entered into the inside (concave side) of the curved and deformed optical portion 18, the intraocular lens 12 is extruded from the tip end side opening part 68 of the nozzle part 56 and inserted into the eye.

As described above, with the intraocular lens insertion device 10, in a state sliding under the step surface 86 formed on the plunger 16, the haptic 20b is made to be pushed to the optical portion 18, so it is possible to inhibit displacement of the haptic 20b in the direction for which the optical portion 18 is convex (concave groove 32 opening side). As a result, when the optical portion 18 goes to a mountain fold state, it is possible to enter the haptic 20b into the optical portion 18 concave side (inside).

In particular, with the lid unit 48 in a closed state, the haptic 20b is pushed to the lens placement surface 34 side by the two pressing parts 54, 54, so before the start of extrusion of the intraocular lens 12 by the plunger 16, it is possible to position the haptic 20b further to the lens placement surface 34 side than the step surface 86. Therefore, when extrusion of the intraocular lens 12 by the plunger 16 starts, it is possible for the haptic 20b to reliably slide under the step surface 86. As a result, it is possible to effectively suppress the upward displacement of the haptic 20b.

Also, when the intraocular lens 12 is extruded by the plunger 16, the optical portion 18 is curved and deformed to a mountain fold state, so it is not necessary to curve and deform the optical portion 18 to a mountain fold state in advance and set the intraocular lens 12 in the stage 30. Thus, the work of setting the intraocular lens 12 in the stage 30 is easier.

Also, compared to a three-piece structure intraocular lens, the intraocular lens 12 has a one-piece structure for which the haptic 20a, 20b volume is large, but the haptic 20b is made to be entered in a relatively large gap formed in the concave side (inside) of the optical portion 18 deformed to a mountain fold state. As a result, even with a one-piece structure intraocular lens 12, it is possible to sufficiently ensure space for the haptic 20b to escape.

Also, compared to a three-piece structure intraocular lens, the intraocular lens 12 has a one piece structure for which the haptics 20a, 20b have low rigidity, but since this is protected so as to have the optical portion 18 wrap the haptic 20b with the haptic 20b deformed to a mountain fold state, it is possible to effectively avoid damage to the haptic 20b.

The deformation guide member is not limited to a constitution consisting of a pair each of the guide rails 76, 76, side rails 78, 78, and the through hole 64 shown with this embodiment. For example, even with a through hole 64 not equipped with the guide rail 76 or side rail 78, by suitably setting the change mode of the cross section shape, extrusion direction or the like, it is also possible to constitute a deformation guide member which folds and deforms the intraocular lens 12 into a mountain shape, and it is possible to constitute a deformation guide member by partially forming convex parts or concave parts inside the through hole 64 or the like.

Figure 21A:
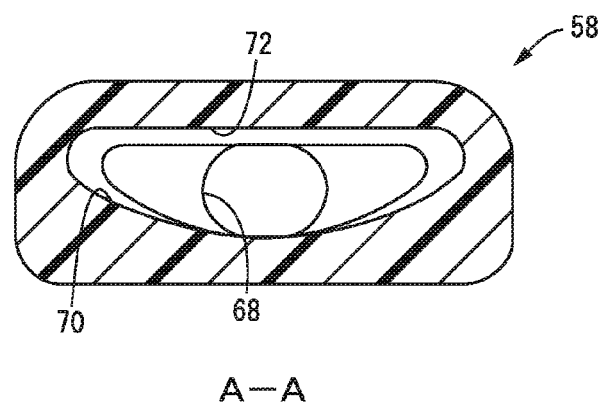
FIGS. 21A-21C are horizontal cross section views for describing another mode of the deformation guide member that can be used with the present invention, and are cross section views of A-A to C-C in FIG. 5.
Figure 21B:
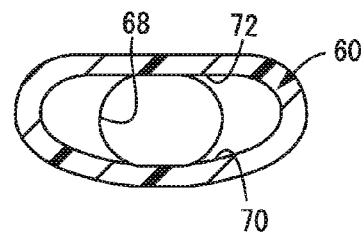
Figure 21C:
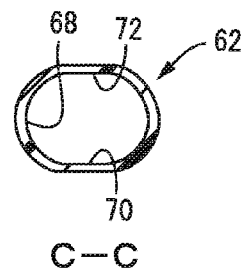

Also, the deformation guide member can be not only the item for which the optical portion 18 is deformed into a mountain folded state as described above, but can also be an item for which the optical portion 18 is deformed to a valley fold state for which a valley line for which the optical portion back surface 24 is made convex toward the bottom surface 70 positioned at the bottom of the height direction extends in the intraocular lens 12 moving direction. As a deformation guide member that realizes a valley fold state, for example as shown in FIGS. 21A-21C, it is possible to use a through hole of a cross section shape for which the through hole 64 of the aforementioned embodiment is vertically inverted, or the like.

Figure 22:
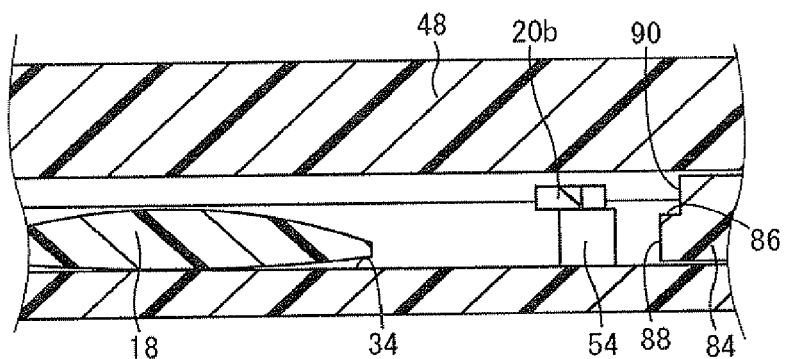
FIG. 22 is an explanatory cross section view for describing a mode of the pressing part and the tip part of the plunger when using the deformation guide member shown in FIGS. 21A-21C.

When using this deformation guide member, if the pressing part 54 is provided, as shown in FIG. 22, the pressing part 54 is provided projecting on the lens placement surface 34. The haptic 20b is pressed upward in the height direction (concave groove 32 opening side), and it is possible to displace the haptic 20b to the top side before extrusion by the plunger 16. To make relative displacement of the haptic 20b to the top side in relation to the optical portion 18 easier, it is also possible to push the optical portion 18 to the lens placement surface 34 side using left and right guide plate units 50, 50 or the center guide plate unit 52. As the plunger, it is possible to use an item equipped with a tip part of a shape for which the tip part 84 of the aforementioned embodiment is inverted vertically.

If a deformation guide member that realizes the valley fold state of the optical portion 18 is used, the pressing part 54 can also be provided projecting to the base plate part 38 of the support member 36. In this case, an insertion through hole in which the pressing part 54 is inserted is formed on the bottom wall of the concave groove 32, and in a state with the support member 36 attached to the device main unit 14, it is possible to use a method for which the pressing part 54 inserted through the insertion through hole is projected on the lens placement surface 34.

Even in a case of using a deformation guide member that realizes a valley fold state of the optical portion 18, the pressing part 54 is not absolutely necessary. It is also possible to place the haptic 20b on the step surface 86 formed on the tip part 84 of the plunger 16, and to lift the haptic 20b to the top side.

It is also possible to curve and deform the optical portion 18 so as to be convex in the concave groove 32 horizontal width direction outward direction (specifically, leftward or rightward in FIG. 14), using the ridge line extending in parallel with the center axis line of the device main unit 14. In this case, as the deformation guide member, it is possible to use a through hole or the like having a cross section shape such as the through hole 64 of the aforementioned embodiment rotated 90 degrees around the center axis of the device main unit 14. The intraocular lens 12 is set in the stage 30 with the concave groove 32 placed vertically and in a state with the optical portion front surface 22 or the optical portion back surface 24 in a state facing in the outward horizontal width direction of the concave groove 32. For the plunger, it is possible to use an item equipped with a tip part such as with the tip part 84 of the aforementioned embodiment rotated 90 degrees around the center axis. By doing this, displacement of the haptic 20b in the direction for which the optical portion 18 becomes convex is suppressed, and the same as with the aforementioned embodiment, it is possible to enter the haptic 20b in the concave side (inside) of the optical portion 18.

Next, we will describe the intraocular lens insertion device of another embodiment of the present invention. Each of the second through fifth embodiments noted below show examples of another mode of the plunger used with the intraocular lens insertion device of the first embodiment. With each of these embodiments, only the part that is different from the first embodiment is described, and for members and parts having the same constitution as those of the first embodiment, we will describe them using the same code numbers as with the first embodiment.

Figure 23:
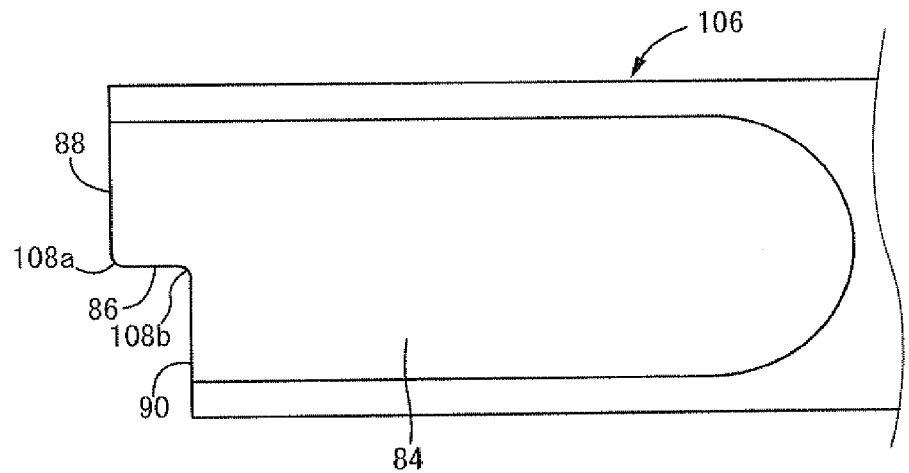
FIG. 23 is an enlarged side view showing the tip part of the plunger used with the intraocular lens insertion device as a second embodiment of the present invention.

FIG. 23 shows the plunger 106 that constitutes the second embodiment of the present invention. This plunger 106 has guide surfaces 108a, 108b that curve in an arc shape with a side surface view (axial right angle direction view corresponding to FIG. 10 of the first embodiment) at the respective boundary part of the step surface 86 and the optical portion pressing surface 88 and the boundary part of the step surface 86 and the haptic pressing surface 90. Note that while the forward guide surface 108a is a ¼ circumference arc cross section which is convex outward, the back guide surface 108b is a ¼ circumference arc cross section which is concave outward.

With an intraocular lens insertion device equipped with this kind of plunger 106, before extrusion of the intraocular lens 12 by the plunger 106, even if the haptic 20b is further to the top side than the step surface 86, the haptic 20b is guided toward the engaging part by the guide surface 108a. Specifically, the plunger 106 advances forward, and if the haptic 20b makes contact with the forward guide surface 108a, by the haptic 20b sliding on the guide surface 108a, the haptic 20b moves to below the step surface 86. By doing this, it is possible to inhibit displacement of the haptic 20b upward.

Also, when the plunger 106 extrudes the intraocular lens 12, after the haptic 20b slides on the step surface 86, by sliding on the back guide surface 108b, the haptic 20b contacts the haptic pressing surface 90 at a position separated downward from the step surface 86. By doing this, it is possible to push the haptic 20b in a state further approaching the lens placement surface 34. As a result, it is even easier to enter the haptic 20b to the optical portion back surface 24 side of the optical portion 18.

Figure 24:
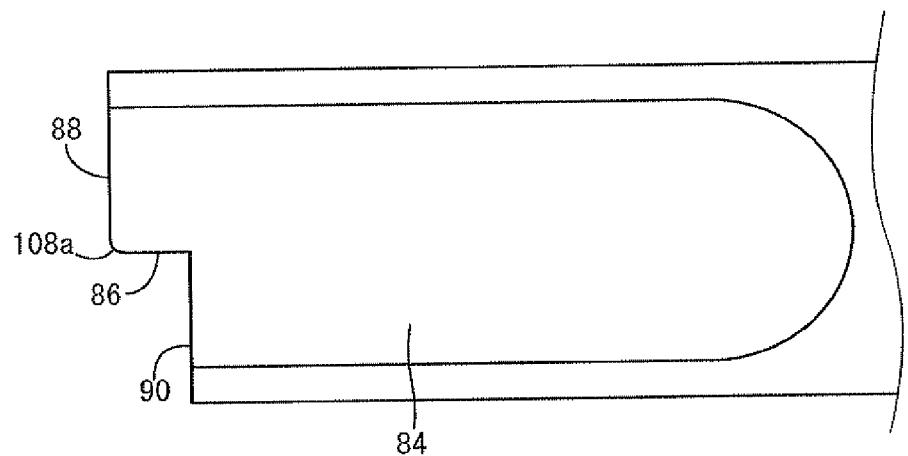
FIG. 24 is a side view for describing another mode of the guide surface that can be used with this embodiment.

It is not necessary to form the guide surfaces 108a, 108b both at the front end and the back end of the step surface 86. For example, as shown in FIG. 24, it is also possible to form only the forward guide surface 108a. In this case, the pressing part 54 of the first embodiment is not provided, and even if the haptic 20b is not displaced approaching the lens placement surface 34 side in advance, entering the haptic 20b to below the step surface 86 is easy.

Figure 25:
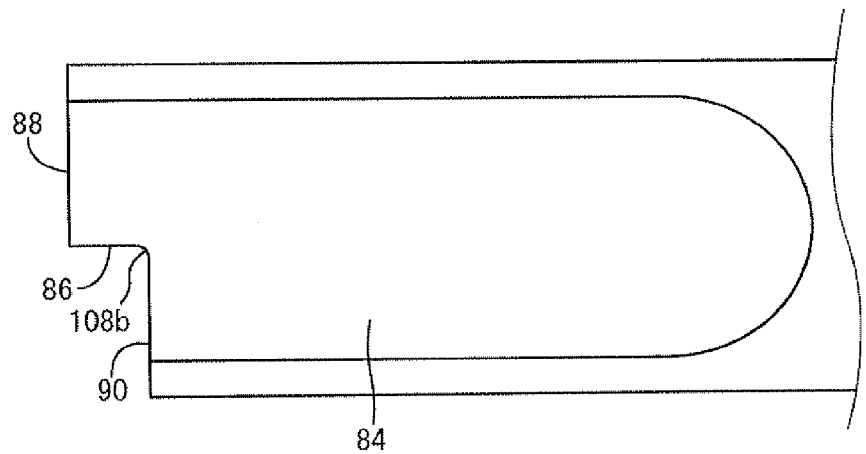
FIG. 25 is a side view for describing another mode of the guide surface that can be used with this embodiment.

Also, as shown in FIG. 25, it is possible to form only the back guide surface 108b. In this case, it is possible to have the haptic 20b even further approach the lens placement surface 34, so even in a case when there is not sufficient floating of the optical portion 18 from the lens placement surface 34 based on the buoyancy due to the lubricant injected from the injection hole 104, or a case when the haptic 20b is not sufficiently pushed by the pressing part 54 or the like, it is easy to have the haptic 20b entered into the optical portion back surface 24 side of the optical portion 18.

Figure 26:
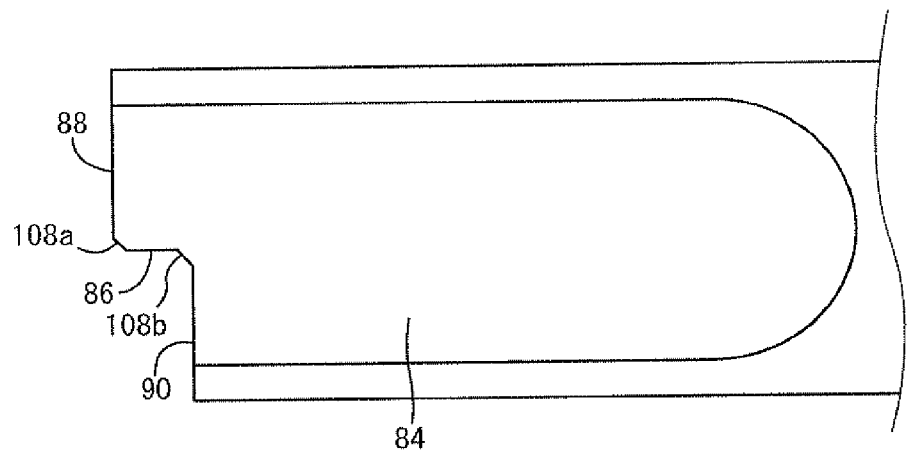
FIG. 26 is a side view for describing another mode of the guide surface that can be used with this embodiment.

Also, as long as the guide surfaces 108a, 108b are items for which it is possible to induct the haptic 20b, it is not necessary to curve in an arc shape with the side view as shown in FIG. 23. For example, as shown in FIG. 26, it is also possible to use a tilted surface facing downward gradually in the drawing as it goes in the backward axial direction as the guide surfaces 108a, 108b.

Figure 27:
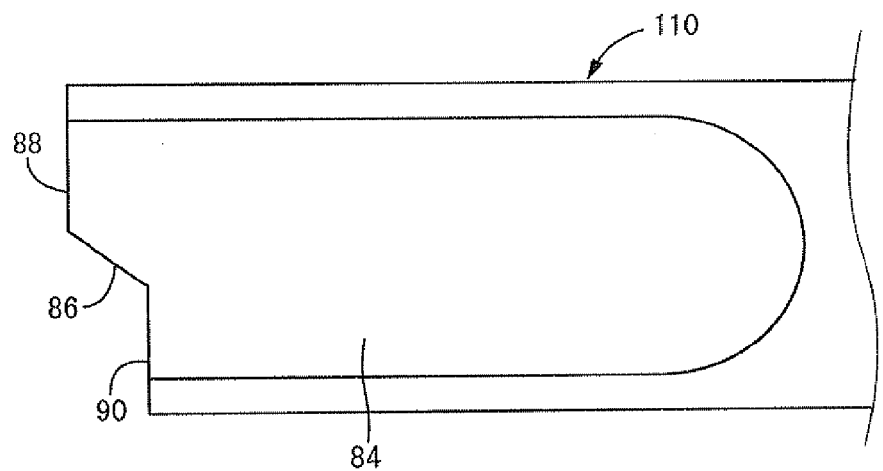
FIG. 27 is an enlarged side view of the tip part of the plunger used with the intraocular lens insertion device as a third embodiment of the present invention.

Next, FIG. 27 shows a plunger 110 constituting the third embodiment of the present invention. With this plunger 110, a gradual tilt is given at the step surface 86 facing the height direction downward as it goes to the back from the axial forward direction.

With an intraocular lens insertion device equipped with this kind of plunger 110, when the intraocular lens 12 is extruded by the plunger 110, by part of the extrusion force acting on the haptic 20b, the haptic 20b slides on the step surface 86 and approaches the lens placement surface 34. Therefore, the haptic 20b is more reliably entered to the optical portion back surface 24 side of the optical portion 18.

Figure 28:
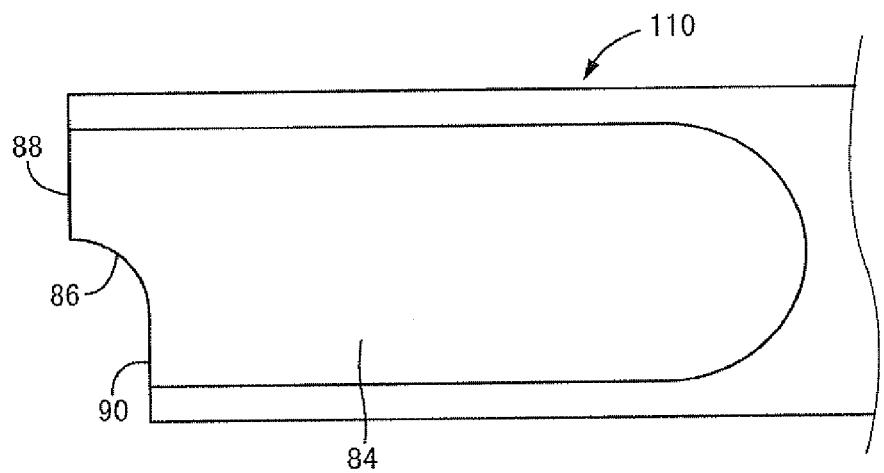
FIG. 28 is a side view for describing another mode of the step surface that can be used with this embodiment.

The step surface 86 having the guide function as described above is not limited to the item noted in FIG. 27. For example, as shown in FIG. 28, it is also possible to be a step surface 86 curved in an arc shape with a side view.

Figure 29:
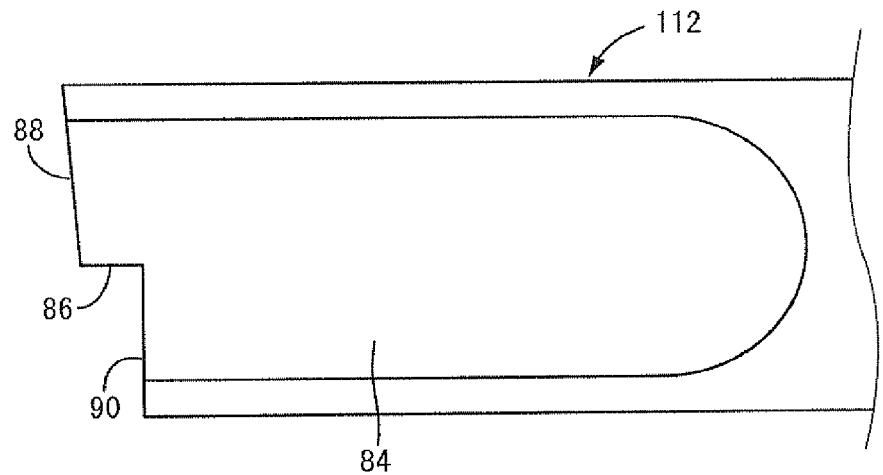
FIG. 29 is an enlarged side view of the tip part of the plunger used with the intraocular lens insertion device as a fourth embodiment of the present invention.

Furthermore, FIG. 29 shows a plunger 112 constituting the fourth embodiment of the present invention. This plunger 112 has a tilt given to the optical portion pressing surface 88 gradually facing downward as it goes in the backward axial direction.

With an intraocular lens insertion device equipped with this kind of plunger 112, even if the haptic 20b is not positioned further to the lens placement surface 34 side than the step surface 86 in advance, by the haptic 20b in contact with the optical portion pressing surface 88 sliding on the optical portion pressing surface 88 and displaced downward based on the partial force action of the contact force, the haptic 20b is entered at the bottom of the step surface 86.

Figure 30:
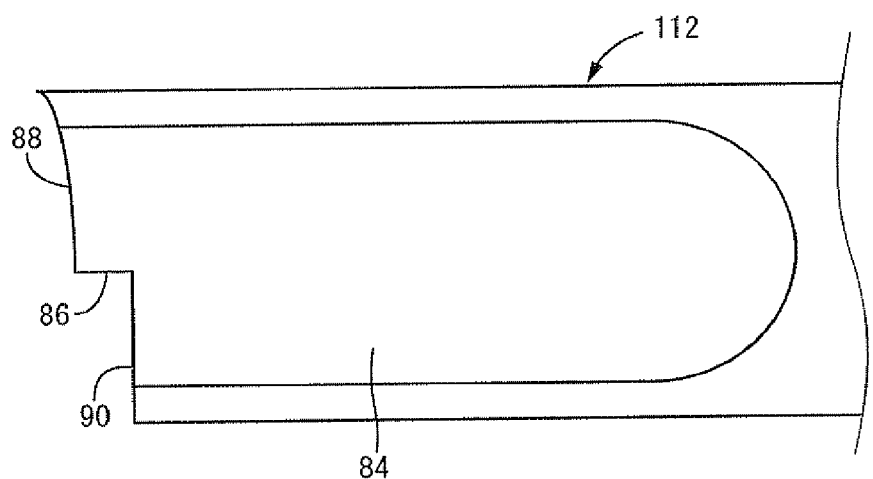
FIG. 30 is a side view for describing another mode of the projection end surface that can be used with this embodiment.

The optical portion pressing surface 88 having the guide function as described above is not limited to the items shown in FIG. 29. For example, as shown in FIG. 30, it is also possible to be an optical portion pressing surface 88 that curves in an arc shape with a side view.

Figure 31:
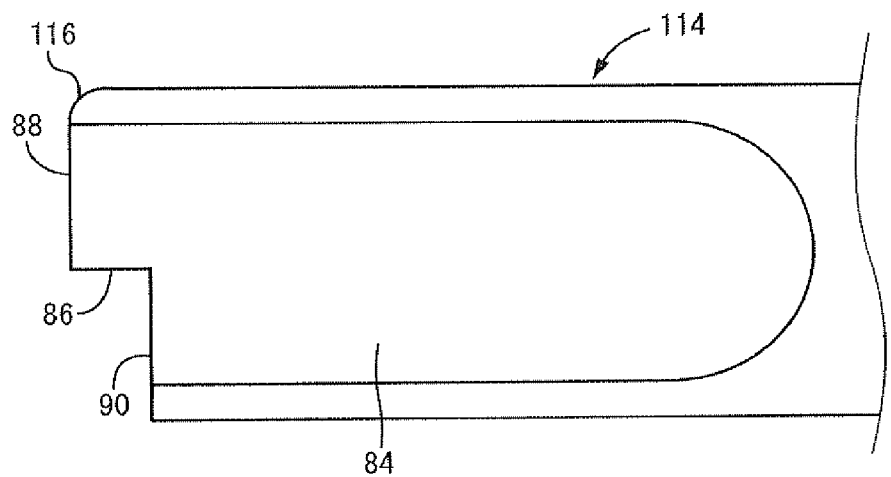
FIG. 31 is an enlarged side view of the tip part of the plunger used with the intraocular lens insertion device as a fifth embodiment of the present invention.
Figure 32:
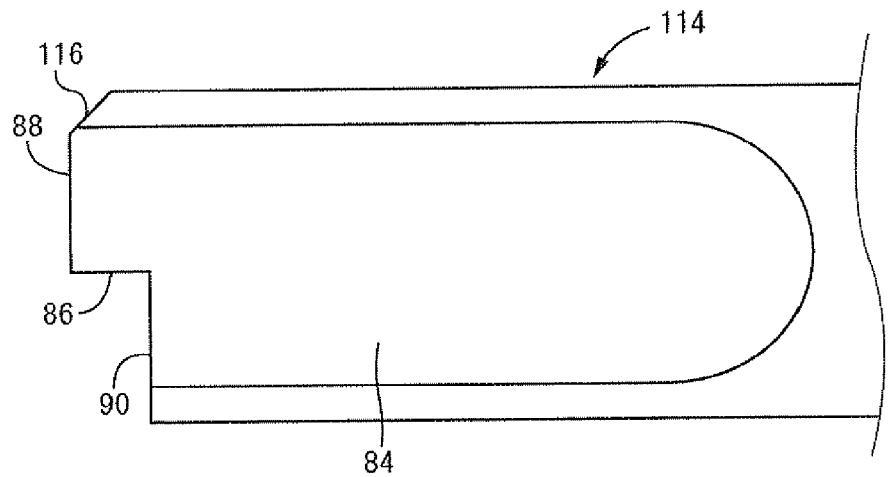
FIG. 32 is a side view for describing another mode of the projection end surface that can be used with this embodiment.

Also, FIG. 31 shows a plunger 114 constituting the fifth embodiment of the present invention. This plunger 114 has a guide surface 116 curved in an arc shape which is convex outward with a side view formed at the forward top end part of the tip part 84. As shown in FIG. 32, this guide surface 116 can also be a tilted surface of a chamfered shape tilted gradually upward as it goes from front to back with a side view.

By using a plunger 114 for which this kind of guide surface 116 is formed, catching is prevented when doing a push operation of the plunger 114 in relation to the intraocular lens insertion device, and it is possible to extrude the intraocular lens more smoothly.

Figure 33:
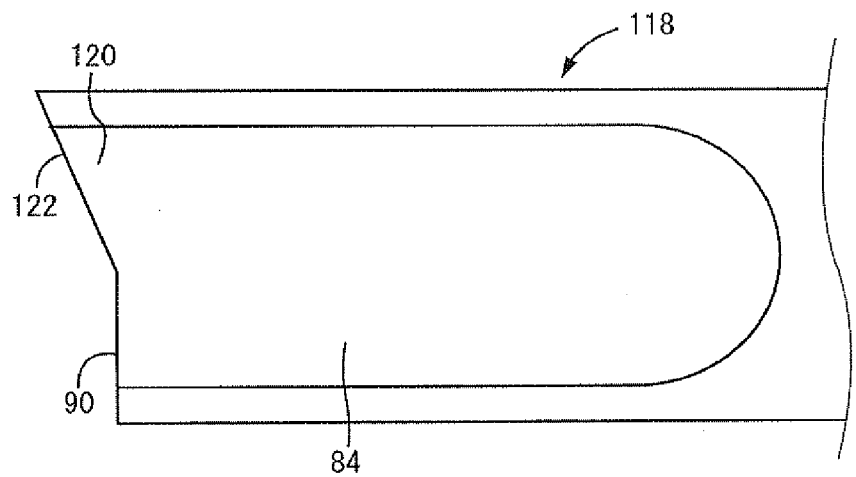
FIG. 33 is an enlarged side view of the tip part of the plunger used with the intraocular lens insertion device as a sixth embodiment of the present invention.

Furthermore, in FIG. 33, a plunger 118 constituting the sixth embodiment of the present invention is shown. This plunger 118 has the engaging projecting part 120 formed as a single unit as the engaging part projecting in the forward axial direction of plunger 118 in the area of roughly half the top side in the height direction of the tip part 84.

The engaging projecting part 120 has a roughly right triangle shape with a side view, and the side surface 122 as an optical portion pressing surface constituting the oblique side from the side view is a tilted surface as it gradually moves downward from front to back. Then, this side surface 122 constitutes a tip surface in the area of roughly half the top side in the height direction of the tip part 84 of the plunger 118. The area that is roughly the bottom half of the height direction of the tip part 84 of the plunger 118, the same as with the first embodiment, is the haptic pressing surface 90 having a plane shape that broadens in the axial right angle direction of the plunger 118.

With an intraocular lens insertion device equipped with this kind of plunger 118, when the intraocular lens 12 is extruded using the plunger 118, the haptic 20b in contact with the side surface 122 of the engaging projecting part 120 slides downward on the side surface 122 by the action of the partial contact force to cause displacement. Thus, the haptic 20b moves to the lens placement surface 34 side. As a result, the haptic 20b more easily enters the inside (concave side) of the curved and deformed optical portion 18.

Figure 34:
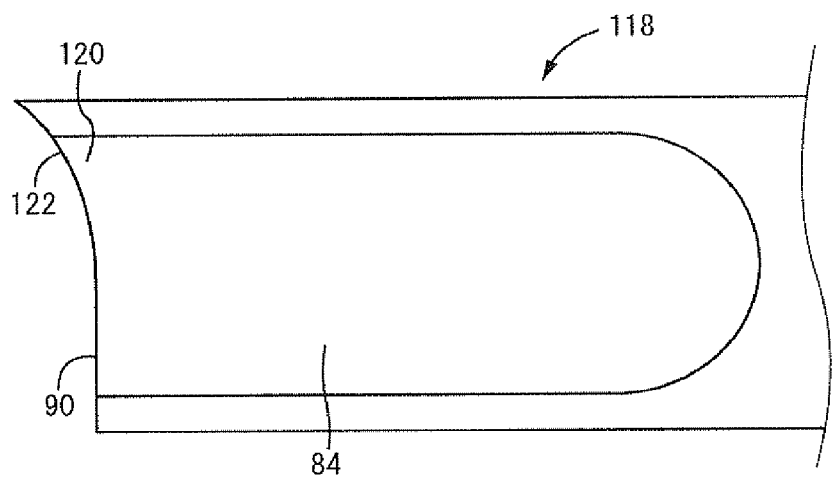
FIG. 34 is a side view for describing another mode of the projection end surface that can be used with this embodiment.

The side surface 122 of the engaging projecting part 120 having the guide function as described above is not limited to the item shown in FIG. 33. For example, as shown in FIG. 34, it is also possible to have an item curved in an arc shape that is concave outward with a side view.

Figure 35:
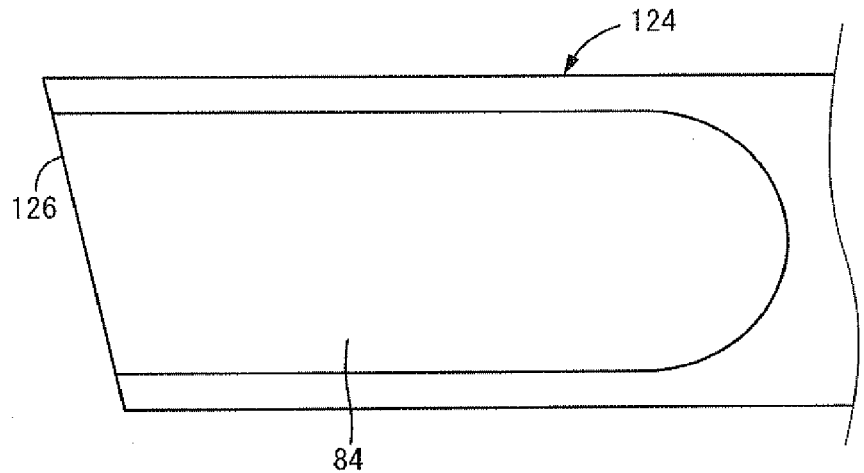
FIG. 35 is an enlarged side view of the tip part of the plunger used with the intraocular lens insertion device as a seventh embodiment of the present invention.

Also, FIG. 35 shows a plunger 124 constituting the seventh embodiment of the present invention. This plunger 124 is a tilted surface that gradually faces downward as the tip surface 126 as an optical portion pressing surface (upper part thereof) and a haptic pressing surface (lower part thereof) goes from front to back across the overall tip part 84. Also, the engaging part is constituted by this tip surface 126.

With the an intraocular lens insertion device equipped with this kind of plunger 124, when the intraocular lens 12 is extruded using the plunger 124, the haptic 20b in contact with the tip surface 126 slides in the downward direction on the tip surface 126 by the action of the partial contact force and is displaced. The haptic 20b moves to the lens placement surface 34 side. As a result, it is easier for the haptic 20b to enter the inside (concave side) of the curved and deformed optical portion 18.

Figure 36:
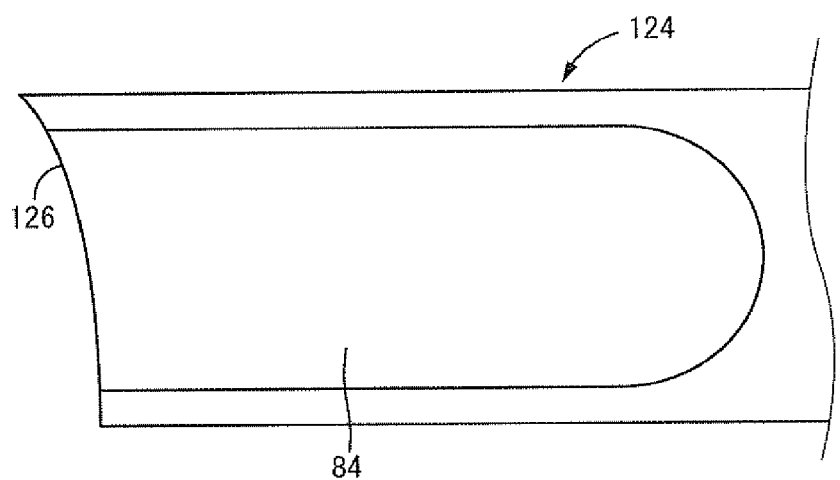
FIG. 36 is a side view for describing another mode of the projection end surface that can be used with this embodiment.

The tip surface 126 of the tip part 84 having the guide function as described above is not limited to the item shown in FIG. 35. For example, as shown in FIG. 36, the tip surface 126 of the tip part 84 can also have a shape curved in an arc with a side view.

While the embodiments of the present invention has been described in detail, the present invention is not limited to those specific notations.

For example, with the aforementioned embodiments, the support member 36 was removably attached to the stage 30 of the device main unit 14, and with the acting projections 40a, 40a, 40b, 40b of this support member 36, the intraocular lens 12 was lifted up and set in a state avoiding contact with the optical portion 18 as much as possible, but this kind of support member 36 is not essential for the present invention. In specific terms, it is also possible to directly place and set the intraocular lens 12 on the lens placement surface 34 of the stage 30 without providing the through holes 44a, 44a, 44b, 44b on the stage 30 of the device main unit 14, and without using the support member 36.

Also, when not using this support member 36, rather than providing the intraocular lens 12 in a state set in advance and wrapped, it is preferable to provide the intraocular lens 12 wrapped separately from the intraocular lens insertion device 10 and to unwrap it when doing a procedure, and to house and set it on the lens placement surface 34 of the stage 30 of intraocular lens insertion device 10. This makes it possible to avoid problems due to direct contact stress being applied over a long time with the storage and distribution processes for the lens placement surface 34 in relation to the optical portion 18 of the intraocular lens 12.

Even when using the support member 36, for example when contacting the optical portion 18 of the intraocular lens 12 or the middle part or tip part of the extension direction of the haptics 20a, 20b or the like, it is possible to form acting projection parts at positions supporting those or the like.

The shape and configuration of the device main unit 14 stage 30 or insertion tube part (nozzle parts 56) or the like that determine the variation modes of the intraocular lens optical portion are items suitably set according to the deformation target shape when inserting the intraocular lens into the eye, and for example including whether or not the guide rails 76, 76 or the side rails 78, 78 or the like are used, is not limited to the items noted in the embodiments. Specifically, the mode of deforming the intraocular lens to be small when inserting it is not limited to the mountain fold state or valley fold state as described previously, and there are many varieties as is well known in the prior art, and in specific terms, can be used with a variation such as being rolled up round or the like, and the various constitutions of the known prior art can be used for the intraocular lens insertion device of the present invention according to the target variation shape.

Also, with the aforementioned embodiments, the intraocular lens 12 was placed flat on the lens placement surface 34 in a free state, but when setting the intraocular lens 12 in the stage 30, it is also possible to have the optical portion 18 in a mountain fold state with a ridge line extending in the axial direction of the device main unit 14 or a valley fold state with a valley line extending in the axial direction of the device main unit 14. As a method of setting the optical portion 18 to a mountain fold state or valley fold state in advance, for example, it is possible to use one whereby the groove width dimension of the concave groove 32 formed on the stage 30 is made small or the like.

KEYS TO SYMBOLS

10: Intraocular lens insertion device, 12: Intraocular lens, 14: Device main unit, 16: Plunger, 18: Optical portion, 20a: Haptic, 20b: Haptic, 30: Stage, 54: Pressing part, 56: Nozzle part (insertion tube part), 64: Through hole (deformation guide member), 76: Guide rail (deformation guide member, deformation guide part), 78: Side rail (deformation guide member, deformation guide part), 86: Step surface (engaging part)

The invention claimed is:

1. An intraocular lens insertion device comprising:
   a tube shaped device main unit;
   a plunger to be inserted into the device main unit from a back side in an axial direction of the device main unit and attached to the device main unit;
   a stage provided in an intermediate part of the axial direction of the device main unit, on which is set on a lens placement surface of the stage an intraocular lens having a pair of haptics projecting from an optical portion, with the pair of haptics in a state extending from the optical portion and facing forward and backward in the axial direction of the device main unit; and a tapered insertion tube part formed facing a front side in the axial direction from the stage so that the intraocular lens set on the lens placement surface of the stage is able to be inserted into an eye by being moved in an axial forward direction of the device main unit by the plunger and by being transformed to be smaller and extruded through the insertion tube part;

wherein the stage includes a concave groove extending in the axial direction, and the lens placement surface comprises a bottom surface of the concave groove, wherein the device main unit includes a deformation guide member that folds and deforms the optical portion of the intraocular lens so as to become concave toward an opening side of the concave groove, and the guide member is constituted by a through hole of the insertion tube part, the through hole having a bottom surface of concave shape toward the opening side and a top surface of a flat surface, wherein a tip part of the plunger that presses the intraocular lens is provided with an optical portion pressing surface for pressing the optical portion, and a haptic pressing surface for pressing the haptic extending from the optical portion in an axial backward direction of the device main unit, wherein the optical portion pressing surface is located further away from the opening side of the concave groove than the haptic pressing surface, and the optical portion pressing surface is positioned forward in the axial direction with respect to the haptic pressing surface, such that a step surface with an axial dimension smaller than a width dimension of the haptic is provided in between the optical portion pressing surface and the haptic pressing surface, and wherein the step surface is configured to be engaged with the haptic pressed by the haptic pressing surface, suppressing displacement of the haptic to a side of the lens placement surface, and the axial dimension of the step surface smaller than the width dimension of the haptic makes the haptic pressing surface close to the optical portion pressing surface in the axial direction so as to enter the haptic into a concave side of the optical portion, the intraocular lens insertion device further comprising a lid unit connected to the stage, wherein in a closed position the lid unit covers the opening side of the concave groove, and wherein the lens placement surface or a base plate part of a support member supporting the stage includes a pressing part projecting therefrom, the pressing part contacting one of the pair of haptics of the intraocular lens when the lid unit is in the closed position.

* * * * *